US009233980B2

(12) United States Patent
Kawanami

(10) Patent No.: US 9,233,980 B2
(45) Date of Patent: Jan. 12, 2016

(54) PROCESS FOR PREPARING A COMPOUND BY A NOVEL SANDMEYER-LIKE REACTION USING A NITROXIDE RADICAL COMPOUND AS A REACTION CATALYST

(71) Applicant: DAIICHI SANKYO COMPANY, LIMITED, Tokyo (JP)

(72) Inventor: Koutarou Kawanami, Hiratsuka (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

(21) Appl. No.: 13/756,939

(22) Filed: Feb. 1, 2013

(65) Prior Publication Data

US 2013/0144061 A1 Jun. 6, 2013

Related U.S. Application Data

(63) Continuation of application No. PCT/JP2011/067408, filed on Jul. 29, 2011.

(30) Foreign Application Priority Data

Aug. 4, 2010 (JP) ................................. 2010-175250
Aug. 4, 2010 (JP) ................................. 2010-175251

(51) Int. Cl.
| | | |
|---|---|---|
| C07D 471/02 | (2006.01) | |
| C07D 491/02 | (2006.01) | |
| C07D 498/02 | (2006.01) | |
| C07D 513/02 | (2006.01) | |
| C07D 515/02 | (2006.01) | |
| A61K 31/44 | (2006.01) | |
| C07D 513/04 | (2006.01) | |
| C07C 201/12 | (2006.01) | |
| C07C 253/30 | (2006.01) | |

(52) U.S. Cl.
CPC ............ *C07D 513/04* (2013.01); *C07C 201/12* (2013.01); *C07C 253/30* (2013.01)

(58) Field of Classification Search
None
See application file for complete search history.

(56) References Cited

U.S. PATENT DOCUMENTS

| 5,424,431 A | 6/1995 | Ohta et al. | |
| 7,547,786 B2 * | 6/2009 | Nagasawa ............ | C07D 513/04 546/114 |
| 2005/0245565 A1 | 11/2005 | Ohta et al. | |
| 2006/0252837 A1 | 11/2006 | Ohta et al. | |

FOREIGN PATENT DOCUMENTS

| EP | 1 415 992 | 5/2004 |
| EP | 1 683 800 | 7/2006 |
| EP | 2 407 450 | 1/2012 |
| JP | 2001-294572 | 10/2001 |
| WO | 92/07849 | 5/1992 |
| WO | 01/83455 | 11/2001 |
| WO | 03/000680 | 1/2003 |
| WO | 03/016302 | 2/2003 |
| WO | 2004/058715 | 7/2004 |
| WO | 2005/047296 | 5/2005 |
| WO | 2009/114589 | 9/2009 |

OTHER PUBLICATIONS

Simeon, FG. et al. Efficient and Regioselective Halogenations of 2-Amino-1,3-thiazoles with Copper Salts. J. Org. Chem. 2009, vol. 74, p. 2579.*
Simeon, FG. et al. Efficient and Regioselective Halogenations of 2-Amino-1,3-thiazoles with Copper Salts. J. Org. Chem. 2009, vol. 74, p. 257.*
Suzuki, N., et al., "Synthetic Reactions in Polyethylene Glycol, Diazotization and Sandmeyer Reactions of Anilines in Polyethylene Glycol-Methylene Dichloride", J. Chem Soc., Chem. Commun., pp. 1523-1524. Japan (1984).
Doyle, N.P., et al. "Alkyl Nitrite-Metal Halide Deamination Reactions . . . ", J. Org. Chem., vol. 42, No. 14, pp. 2426-2431 (1977).
Nonhebel, D.C., et al., "A Study of the Mechanism of the Sandmeyer Reaction", Dyson Perrins Laboratory, Oxford University, May 8, pp. 16-27. Europe (1957).
Jauch, J., "A Short Total Synthesis of Kuehneromycin A", Angew. Chem Int. Ed. 39, No. 15, pp. 2764-2765 (2000).
De Mico, A., et al., "A Versatile and Highly Selective Hypervalent Iodine (III)/2,2,6,6-tetramethyl-1-piperidinyloxyl-mediated oxidation of alcohols to carbonyl compounds", J. Org. Chem. vol. 62, No. 20, pp. 6974-6977. Italy (1997).
Einhorn, J., et al., "Efficient and Highly Selective Oxidation of Primary Alcohols to Aldehydes by N-chlorosuccinimide mediated by oxoammonium salts" J. Org. Chem. vol. 61, No. 21, pp. 7452-7454. France (1996).
Simeon, F.G., et al., "Efficient and Regioselective Halogenations of 2-Amino-1,3-thiazoles with Copper Salts", J. Org. Chem. vol. 74, No. 6, pp. 2578-2580. U.S. (2009).
Heinrich, M.R., et al., "Intermolecular Radical Carboaminohydroxylation of Olefins with Aryl Diazonium Salts and TEMPO" Organic Letters, American Chemical Society, vol. 9, No. 19, pp. 3833-3835. Germany (2007).
Beletskaya, I.P., et al., "Catalytic Sandmeyer Bromination", Synthesis, No. 16, pp. 2534-2538. Russia (2007).
Sandmeyer, T., "Uber die Ersetzung der Amidgruppe durch Chlor, Brom und Cyan in den aromatischen Substanze" Chemische Berichteu, Nov. 13, pp. 2650-2653 (1884) (machine-translated English abstract submitted).
Balz, G., et al, Ber. Dtsch. Chem. Ges., 60, pp. 1186-1190 (1927) (machine-translated English abstract submitted).

(Continued)

*Primary Examiner* — Janet L Andres
*Assistant Examiner* — Ben S Michelson
(74) *Attorney, Agent, or Firm* — Locke Lord LLP

(57) ABSTRACT

The present invention provides a novel process for preparing a substituted aromatic compound such as an aromatic halo compound or a salt thereof through a transformation reaction of an aromatic diazonium salt from an aromatic amino compound at stable high yields utilizing a novel Sandmeyer-like reaction using a nitroxide radical compound as a reaction catalyst.

14 Claims, No Drawings

(56) References Cited

OTHER PUBLICATIONS

Extended European Search Report issued in corresponding EP Application No. 11814558.0, dated Dec. 4, 2013.
Ochiai, E., "Recent Japanese Work on the Chemistry of Pyridine 1-Oxide and Related Compounds," The Journal of Organic Chemistry, vol. 18, No. 5, May 1, pp. 534-551 (1953).
Lee, Y.M., et al., "Efficient and Economic Halogenation of Aryl Amines via Arenediazonium Tosylate Salts," Tetrahedron, vol. 66, No. 37, pp. 7418-7422, Jul. 21, 2010.
International Search Report issued in corresponding PCT Application No. PCT/JP2011/067408, dated Nov. 1, 2011.
Written Opinion of the International Searching Authority issued in corresponding PCT Application No. PCT/JP2011/067408, dated Nov. 1, 2011.
International Preliminary Report on Patentability issued in corresponding PCT Application No. PCT/JP2011/067408, dated Mar. 12, 2013.

\* cited by examiner

PROCESS FOR PREPARING A COMPOUND BY A NOVEL SANDMEYER-LIKE REACTION USING A NITROXIDE RADICAL COMPOUND AS A REACTION CATALYST

This application is a continuation of International Application No. PCT/JP2011/067408, filed on Jul. 29, 2011, entitled "PROCESS FOR PREPARING A COMPOUND BY A NOVEL SANDMEYER-LIKE REACTION USING A NITROXIDE RADICAL COMPOUND AS A REACTION CATALYST", which claims the benefit of Japanese Patent Application Number JP 2010-175250, filed on Aug. 4, 2010 and Japanese Patent Application Number JP 2010-175251, filed on Aug. 4, 2010, all of which are hereby incorporated by reference.

FIELD OF INVENTION

The present invention relates to a novel industrial process for preparing a substituted aromatic compound such as an aromatic halo compound by a novel Sandmeyer-like reaction using a nitroxide radical compound as a reaction catalyst.

BACKGROUND OF THE INVENTION

The processes shown below are known as processes for preparing a substituted aromatic compound such as an aromatic halo compound through a transformation reaction of an aromatic diazonium salt from an aromatic amino compound.

A process for preparing a cyanobenzene derivative, comprising treating an aniline derivative (A) with a diazotization reagent and treating the benzenediazonium salt derivative (B) formed with a monovalent copper catalyst such as copper (I) cyanide (C-1) is based on a known Sandmeyer reaction or its analogous reaction (Sandmeyer-like reaction), as shown in the following scheme (see e.g., Patent References 1 to 2 and Non Patent References 1 to 5):

[Formula 1]

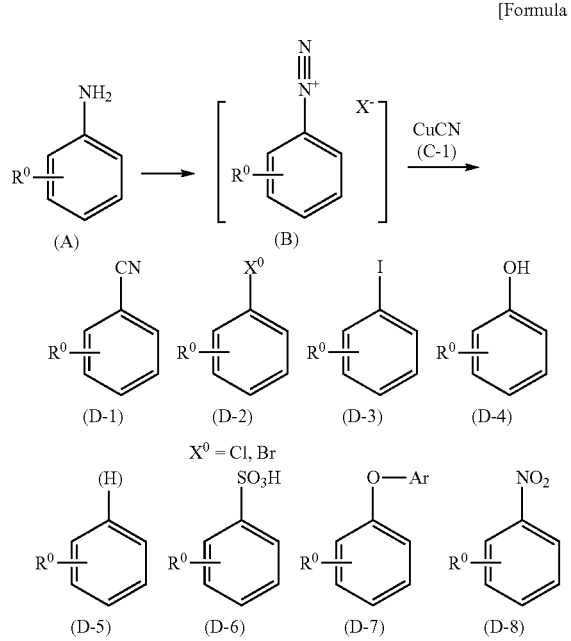

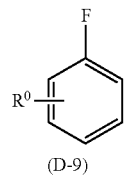

(D-9)

wherein $X^-$ represents the counter anion of the diazonium salt; and $R^0$ represents a hydrogen atom or one or more substituents on the benzene ring.

Since the aromatic diazonium salt (B) obtained by the diazotization of aniline derivative (A) is generally an unstable and highly reactive intermediate, this well-known Sandmeyer reaction or its analogous reaction involves treating the aromatic diazonium salt (B) with a source material for substituents such as hydrogen chloride, hydrogen bromide, potassium iodide, sodium iodide, hydrogen cyanide, sodium cyanide, potassium cyanide, sulfuric acid, potassium sulfite, sodium sulfite, sodium bisulfate, sodium nitrite, potassium nitrite, hypophosphorous acid, or a hydroxyaryl derivative in the presence of a monovalent metal copper catalyst to prepare a substituted aromatic compound (D-2 to D-9) such as an aromatic cyano compound (D-1). In this context, hydrochloride, oxalate, sulfate, nitrate, perchlorate, tetrafluoroborate, hexafluorophosphate, or the like is used as a salt in the aromatic diazonium salt. Hydrochloride, oxalate, or tetrafluoroborate is generally used.

Alternatively, known processes for preparing the desired substituted aromatic compound (D) through a transformation reaction of an aromatic diazonium salt without use of a copper catalyst include: 1) a process for preparing a heteroaromatic halo compound from a heteroaromatic diazo compound in the presence of a source material for halogen such as hydrogen bromide without use of a copper catalyst; and 2) a process for preparing a heteroaromatic hydride compound from a heteroaromatic diazo compound in the presence of hypophosphorous acid without use of a copper catalyst (see e.g., Patent Reference 3).

Nitroxide radical compounds are known as organic free radicals that exist very stably. Such nitroxide radical compounds, typified by 2,2,6,6-tetramethylpiperidine 1-oxyl (TEMPO), represented by the following formula (5j):

[Formula 2]

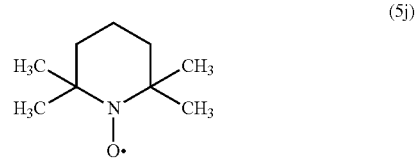

are commercially available as organic synthetic reagents and are used as oxidation reagents, for example, for the oxidation of a primary alcohol into an aldehyde, in organic synthesis (see e.g., Non Patent References 6 to 8).

Use of a nitroxide radical compound in a Sandmeyer reaction or its analogous reaction has previously been reported only in the literature showing that in the course of studies on various conditions including copper catalysts and temperatures as to the synthesis of a halothiazole derivative from an aminothiazole derivative, the ratio and yield of products did not differ between the addition of a nitroxide radical compound 2,2,6,6-tetramethylpiperidine 1-oxyl (TEMPO) and the non-addition thereof (see e.g., Non Patent Reference 9). Thus, only a monovalent copper catalyst is a known catalyst that can promote a transformation reaction of an aromatic diazonium salt during a Sandmeyer reaction or its analogous reaction to prepare a substituted aromatic compound such as an aromatic cyano compound (D-1).

Meanwhile, a substituted aromatic compound prepared by a Sandmeyer reaction or its analogous reaction is often used as an intermediate for pharmaceutical preparation. Compounds shown below can be taken as an example.

A compound represented by the following formula (E) [hereinafter, also referred to as compound (E)]:

[Formula 3]

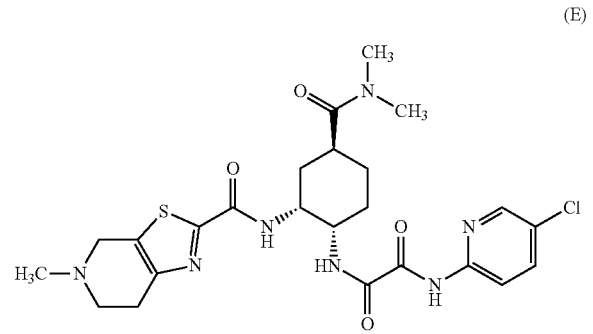

(E)

or a pharmacologically acceptable salt thereof or a hydrate thereof, is a compound that exhibits an FXa inhibitory effect, as disclosed in Patent References 4 to 6, and is useful as a preventive and/or therapeutic drug for thrombotic and/or embolic diseases (see e.g., Patent References 4 to 6). The thiazole derivative 5-methyl-4,5,6,7-tetrahydrothiazolo[5,4-c]pyridine-2-carboxylic acid (13) or a salt thereof is a compound that is important as an intermediate for preparation of FXa inhibitor compound (E) or a pharmacologically acceptable salt thereof, or a hydrate thereof, as shown in the scheme shown below (see e.g., Patent References 4 to 6).

For preparation of compound (13) or a salt thereof, its precursor bromide compound (11a) [compound represented by formula (11) in the scheme shown below wherein $X^{10}$ is a bromine atom] or a salt thereof is important. A Sandmeyer reaction using a monovalent copper catalyst has been reported as a preparation method thereof (see e.g., Patent Reference 7). Alternatively, a copper catalyst-free method (see e.g., Patent Reference 8) has also been reported, but does not offer high reaction yields.

[Formula 4]

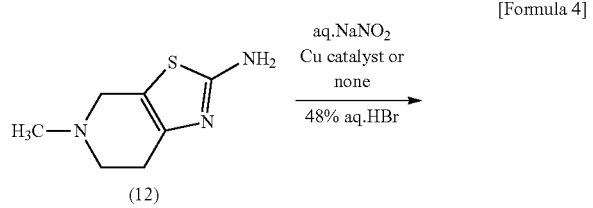

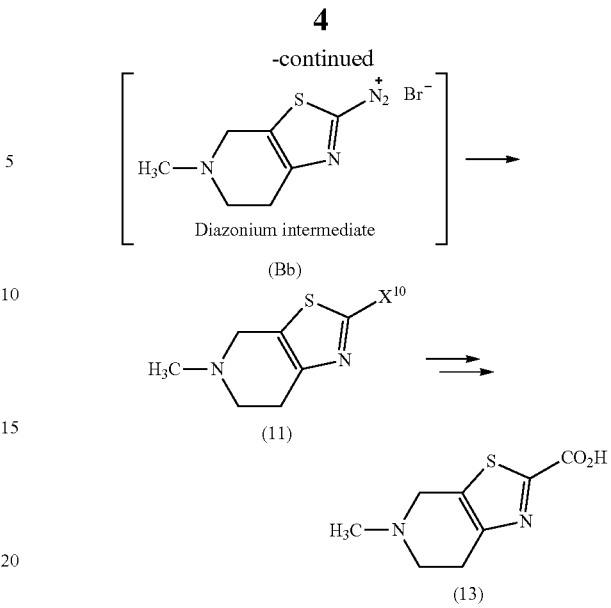

wherein $X^{10}$ represents a halo group.

CITATION LIST

Patent References

Patent Reference 1: International Publication No. WO 1992/07849
Patent Reference 2: Japanese Patent Laid-Open No. 2001-294572
Patent Reference 3: International Publication No. WO 2005/047296
Patent Reference 4: International Publication No. WO 2004/058715
Patent Reference 5: International Publication No. WO 2003/016302
Patent Reference 6: International Publication No. WO 2003/000680
Patent Reference 7: International Publication No. WO 1992/07849
Patent Reference 8: International Publication No. WO 2005/047296

Non Patent References

Non Patent Reference 1: Suzuki Nobutaka et al., Journal of the Chemical Society, Chemical Communications, 22, 1984, 1523-1524.
Non Patent Reference 2: M. P. Doyle et al., Journal of Organic Chemistry, 42, 1977, 2426-2431.
Non Patent Reference 3: Sandmeyer, Chemische Berichte, 17, 1884, 2650.
Non Patent Reference 4: D. C. Nonhebel et al., Proceedings of the Royal Society of London., Series A, Mathematical and Physical Sciences, Vol. 242, No. 1228 (Oct. 8, 1957), 16-27.
Non Patent Reference 5: Balz, G. Schiemann, G., Chem. Ber. 1927, 60, 1186.
Non Patent Reference 6: Jauch, J., Angew. Chem., Int. Ed. 2000, 39, 2764.
Non Patent Reference 7: De Mico, A. et al., J. Org. Chem., 1997, 62, 6974.
Non Patent Reference 8: Einhorn, J. et al., J. Org. Chem., 1996, 61, 7452.
Non Patent Reference 9: F G Simeon et al., J. Org. Chem., Note, 74, 2009, 2578-2580.

SUMMARY OF INVENTION

Technical Problem

The Sandmeyer reaction, which is characterized by using a monovalent copper catalyst, is a well-known reaction for preparing a substituted aromatic compound (D-1 to D-9) such as an aromatic cyano compound (D-1), but presents a problem with the removal of the copper catalyst after completion of the reaction. In particular, for use in large-scale synthesis or methods for preparing pharmaceutical materials, it is required to completely remove the copper catalyst. This removal procedure is complicated and becomes a major obstacle from the viewpoint of liquid waste disposal or environmental preservation. In addition, a Sandmeyer reaction using a monovalent copper catalyst disadvantageously gives low reaction yields, depending on the reactive substrates.

Alternatively, a copper catalyst-free method analogous to the Sandmeyer reaction (see e.g., Patent Reference 3) disadvantageously gives low yields. A further problem found with the copper catalyst-free method is yields varying depending on stirring or reaction temperature. However, an alternative preparation process capable of solving these problems is not yet known.

Thus, an object of the present invention is to find an industrial process for efficiently preparing a substituted aromatic compound (D) such as an aromatic halo compound (D-2) by way of an aromatic diazonium salt from an aromatic amino compound by the transformation reaction of an aromatic diazonium salt.

Solution to Problem

The present inventors have conducted diligent studies to attain the object and consequently completed the present invention by finding that nitroxide radical compounds are very effective for attaining the object.

The present invention provides (1) to (12) shown below.

(1): A process for preparing a substituted aromatic compound represented by the following formula (1) or a salt or a solvate thereof via an aromatic diazonium salt represented by the following formula (3), the substituted aromatic compound having substituent Y introduced in situ at the position of the diazonio group:

[Formula 5]

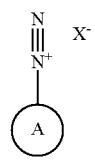

(3)

wherein ring A represented by the following formula (4):

[Formula 6]

(4)

represents an aromatic hydrocarbon ring or an aromatic heterocyclic ring (wherein the aromatic hydrocarbon ring and the aromatic heterocyclic ring may each have 1 to 5 identical or different groups as substituents selected from substituent group α);

substituent group α represents a group consisting of a halo group, a nitro group, a cyano group, a C1-C8 alkyl group, a halo-C1-C8 alkyl group, a C2-C8 alkenyl group, a C2-C8 alkynyl group, a C6-C14 aryl group, a C4-C10 heteroaryl group, a C3-C8 cycloalkyl group, a C1-C8 alkoxy group, a halo-C1-C8 alkoxy group, a C6-C14 aryloxy group, a C1-C7 acyl group, a C2-C7 acyloxy group, a C1-C8 alkoxycarbonyloxy group, a carboxy group, a C1-C8 alkoxycarbonyl group, a carbamoyl group, a mono- or di-C1-C8 alkylcarbamoyl group, a C1-C7 acylamino group, a C1-C8 alkoxycarbonylamino group, a C1-C8 alkylsulfonylamino group, a C1-C8 alkylthio group, a C1-C8 alkylsulfonyl group, and an oxo group;

X⁻ represents the counter anion of the diazonium salt; and the diazonio group is bonded to a carbon atom constituting an element of ring A, and

[Formula 7]

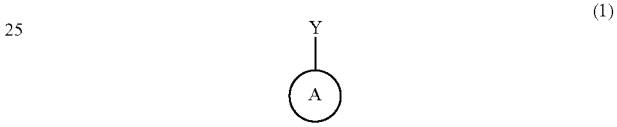

(1)

wherein substituent Y represents a substituent substituted for the diazonio group and is bonded to a carbon atom constituting an element of ring A; and ring A is as defined above, the process comprising treating an aromatic amino compound represented by the following formula (2) or a salt or a solvate thereof:

[Formula 8]

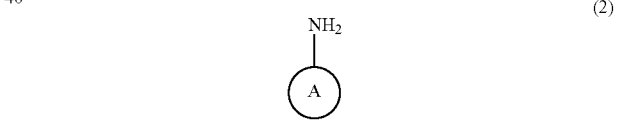

(2)

wherein the amino group is bonded to a carbon atom constituting an element of ring A; and ring A is as defined above, with a diazotization reagent in the presence of a Bronsted acid, a source material for substituent Y, and a nitroxide radical compound in a solvent.

(2): A preparation process according to (1), wherein substituent Y is a halo group, a cyano group, a sulfo group, a hydroxy group, a nitro group, a hydrogen atom, or an aryloxy group.

(3): A preparation process according to (1), wherein substituent Y is a halo group, a cyano group, or a hydroxy group.

(4): A preparation process according to any one of (1) to (3), wherein the source material for substituent Y is hydrogen chloride, hydrogen bromide, potassium iodide, sodium iodide, hydrogen cyanide, sodium cyanide, potassium cyanide, sulfuric acid, potassium sulfite, sodium sulfite, sodium bisulfate, sodium nitrite, potassium nitrite, hypophosphorous acid, or a hydroxyaryl derivative.

(5): A preparation process according to any one of (1) to (3), wherein the source material for substituent Y is hydrogen chloride or hydrogen bromide.

(6): A preparation process according to any one of (1) to (5), wherein the solvent is one or two or more solvents selected from the group consisting of water, C1-C8 alcohol solvents, C2-C4 nitrile solvents, and dimethyl sulfoxide.

(7): A preparation process according to any one of (1) to (6), wherein the Bronsted acid is sulfuric acid, nitric acid, hydrochloric acid, bromic acid, iodic acid, perchloric acid, tetrafluoroboric acid, or hexafluorophosphoric acid.

(8): A preparation process according to any one of (1) to (7), wherein the counter anion of the aromatic diazonium salt represented by X⁻ is chloride, bromide, sulfate, nitrate, perchlorate, tetrafluoroborate, or hexafluorophosphate.

(9): A preparation process according to any one of (1) to (8), wherein the aromatic hydrocarbon ring or the aromatic heterocyclic ring (wherein the aromatic hydrocarbon ring and the aromatic heterocyclic ring may each have 1 to 5 identical or different groups as substituents selected from substituent group α) as ring A represented by the following formula (4):

[Formula 9]

(4)

is a benzene ring, a naphthalene ring, a tetrahydronaphthalene ring, an anthracene ring, a tetrahydroanthracene ring, an octahydroanthracene ring, a phenanthrene ring, a tetrahydrophenanthrene ring, an octahydrophenanthrene ring, a quinoline ring, a dihydroquinoline ring, a tetrahydroquinoline ring, an isoquinoline ring, a dihydroisoquinoline ring, a tetrahydroisoquinoline ring, a quinazoline ring, a dihydroquinazoline ring, a tetrahydroquinazoline ring, a quinoxaline ring, a dihydroquinoxaline ring, a tetrahydroquinoxaline ring, a cinnoline ring, a dihydrocinnoline ring, a tetrahydrocinnoline ring, a phthalazine ring, a dihydrophthalazine ring, a tetrahydrophthalazine ring, a benzotriazine ring, a dihydrobenzotriazine ring, a tetrahydrobenzotriazine ring, an indole ring, an indoline ring, an isoindole ring, an isoindoline ring, a benzoxazole ring, a dihydrobenzoxazole ring, a benzisoxazole ring, a dihydrobenzisoxazole ring, a benzothiazole ring, a dihydrobenzothiazole ring, a benzisothiazole ring, a dihydrobenzisothiazole ring, a benzimidazole ring, a dihydrobenzimidazole ring, a benzopyrazole ring, a dihydrobenzopyrazole ring, a benzotriazole ring, a dihydrobenzotriazole ring, a benzofuran ring, a dihydrobenzofuran ring, a benzothiophene ring, a dihydrobenzothiophene ring, a benzoxadiazole ring, a benzothiadiazole ring, a pyrrole ring, a furan ring, a thiophene ring, an imidazole ring, a pyrazole ring, a triazole ring, a tetrazole ring, an oxazole ring, an isoxazole ring, a triazole ring, an isothiazole ring, an oxadiazole ring, a thiadiazole ring, a pyridine ring, a pyrimidine ring, a pyrazine ring, a pyridazine ring, a triazine ring, a furopyrrole ring, a dihydrofuropyrrole ring, a furothiazole ring, a dihydrofurothiazole ring, a pyranothiazole ring, a dihydropyranothiazole ring, a thienofuran ring, a dihydrothienofuran ring, a thienothiazole ring, a dihydrothienothiazole ring, a pyrrolopyridine ring, a dihydropyrrolopyridine ring, a tetrahydropyrrolopyridine ring, a furopyridine ring, a thienopyridine ring, a dihydrothienopyridine ring, a tetrahydrothienopyridine ring, an oxazolopyridine ring, a dihydrooxazolopyridine ring, a tetrahydrooxazolopyridine ring, an isoxazolopyridine ring, a dihydroisoxazolopyridine ring, a tetrahydroisoxazolopyridine ring, a thiazolopyridine ring, a dihydrothiazolopyridine ring, a tetrahydrothiazolopyridine ring, an isothiazolopyridine ring, a dihydroisothiazolopyridine ring, a tetrahydroisothiazolopyridine ring, an imidazolopyridine ring, a dihydroimidazolopyridine ring, a tetrahydroimidazolopyridine ring, a pyrazolopyridine ring, a dihydropyrazolopyridine ring, a tetrahydropyrazolopyridine ring, a triazolopyridine ring, a dihydrotriazolopyridine ring, a tetrahydrotriazolopyridine ring, a thiazolopyridazine ring, a tetrahydrothiazolopyridazine ring, a pyrrolopyrimidine ring, a dihydropyrrolopyrimidine ring, a naphthyridine ring, a dihydronaphthyridine ring, a tetrahydronaphthyridine ring, a pyridotriazine ring, a dihydropyridotriazine ring, a tetrahydropyridotriazine ring, a pyridopyrazine ring, a dihydropyridopyrazine ring, a tetrahydropyridopyrazine ring, a pyridopyridazine ring, a dihydropyridopyridazine ring, or a tetrahydropyridopyridazine ring; and substituent group α is the group consisting of a halo group, a nitro group, a cyano group, a C1-C8 alkyl group, a halo-C1-C8 alkyl group, a C2-C8 alkenyl group, a C2-C8 alkynyl group, a C6-C14 aryl group, a C4-C10 heteroaryl group, a C3-C8 cycloalkyl group, a C1-C8 alkoxy group, a halo-C1-C8 alkoxy group, a C6-C14 aryloxy group, a C1-C7 acyl group, a C2-C7 acyloxy group, a C1-C8 alkoxycarbonyloxy group, a carboxy group, a C1-C8 alkoxycarbonyl group, a carbamoyl group, a mono- or di-C1-C8 alkylcarbamoyl group, a C1-C7 acylamino group, a C1-C8 alkoxycarbonylamino group, a C1-C8 alkylsulfonylamino group, a C1-C8 alkylthio group, a C1-C8 alkylsulfonyl group, and an oxo group.

(10a): A preparation process according to any one of (1) to (9), wherein the nitroxide radical compound or a salt thereof is a compound represented by the following formula (5) or a salt thereof:

[Formula 10]

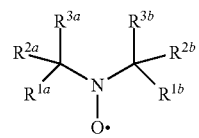

(5)

wherein $R^{1a}$ and $R^{1b}$ are identical or different and each represents a hydrogen atom, a methyl group, or an ethyl group; $R^{2a}$ and $R^{2b}$ 1) are identical or different and each represents a hydrogen atom, a methyl group, or an ethyl group, or
2) together form a 2-azaadamantyl ring with $R^{3a}$ and $R^{3b}$, the carbon atoms bonded to $R^{2a}$, $R^{2b}$, $R^{3a}$, and $R^{3b}$, and the nitrogen atom; and $R^{3a}$ and $R^{3b}$ 3) are identical or different and each represents a hydrogen atom, a methyl group, or an ethyl group,
4) together form a dimethylene group or a trimethylene group [wherein the dimethylene group or the trimethylene group may have one group as a substituent selected from the group consisting of a C1-C3 alkyl group, a hydroxy group, a C1-C3 alkoxy group, a phosphonooxy group, a benzyloxy group, a phenoxy group, a nitro group, a cyano group, a carboxy group, a C1-C3 alkoxycarbonyl group, a carbamoyl group, a N-mono-(C1-C3 alkyl)carbamoyl group, a N,N-di-(C1-C3 alkyl)carbamoyl group, an amino group, a (C2-C5 alkanoyl)amino group, a benzoylamino group, a 2,5-dioxo-pyrrolidin-1-yl group, a 2,5-dioxo-2,5-dihydropyrrol-1-yl group, a (2,5-dioxo-2,5-dihydropyrrol-1-yl) methyl group, an oxo group, and a hydroxyimino group], or 5) together form an ethene-1,2-diyl group (wherein the ethene-1,2-diyl group may have one group as a substituent selected from the group consisting of a C1-C3 alkyl group, a hydroxy-C1-C3 alkyl group, a carboxy group, and a carbamoyl group).

(10b): The preparation process according to (10a), wherein $R^{1a}$ and $R^{1b}$ are identical or different and each represents a hydrogen atom or a methyl group.

(10c): The preparation process according to (10a) or (10b), wherein $R^{2a}$ and $R^{2b}$ are identical or different and each represents a hydrogen atom or a methyl group.

(10d): The preparation process according to any one of (10a) to (10c), wherein $R^{3a}$ and $R^{3b}$ are identical or different and each represents a hydrogen atom or a methyl group.

(10e): The preparation process according to any one of (10a) to (10d), wherein $R^{3a}$ and $R^{3b}$ 4) together form a dimethylene group or a trimethylene group [wherein the dimethylene or trimethylene group may have one group as a substituent selected from the group consisting of a hydroxy group, a C1-C3 alkoxy group, a benzyloxy group, a carboxy group, a carbamoyl group, a N-mono-(C1-C3 alkyl)carbamoyl group, a N,N-di-(C1-C3 alkyl)carbamoyl group, an acetylamino group, a benzoylamino group, a 2,5-dioxo-pyrrolidin-1-yl group, and a 2,5-dioxo-2,5-dihydropyrrol-1-yl group], or 5) together form an ethene-1,2-diyl group (wherein the ethene-1,2-diyl group may have one group as a substituent selected from the group consisting of a C1-C3 alkyl group, a hydroxy-C1-C3 alkyl group, a carboxy group, and a carbamoyl group).

(10f): The preparation process according to any one of (1) to (9), wherein the nitroxide radical compound is one or two or more compounds selected from the group consisting of the following:

3-carboxy-2,2,5,5-tetramethyl-1-pyrrolidine 1-oxyl;

3-carbamoyl-2,2,5,5-tetramethylpyrrolidine 1-oxyl;

3-carbamoyl-2,2,5,5-tetramethyl-3-pyrroline 1-oxyl;

4-oxo-2,2,6,6-tetramethylpiperidinoxyl;

4-hydroxy-2,2,6,6-tetramethylpiperidine 1-oxyl;

4-acetamido-2,2,6,6-tetramethylpiperidine 1-oxyl;

2,2,6,6-tetramethylpiperidine 1-oxyl;

3-(maleimidomethyl)-proxyl;

N-(1-oxyl-2,2,6,6-tetramethyl-4-piperidinyl)maleimide; and 1-methyl-2-azaadamantane N-oxyl; or salts thereof.

(11): A preparation process according to any one of (1) to (10), wherein the amount of the nitroxide radical compound used is stoichiometrically in the range of 0.01 to 0.5 molar equivalents with respect to the reactive substrate organic diazonium salt or organic amino compound or salt or solvate thereof.

(12): Use of a nitroxide radical compound for preparation of a substituted aromatic compound or a salt or a solvate thereof from an aromatic amino compound or a salt or a solvate thereof by a Sandmeyer reaction or an analogous reaction thereof.

The present invention also provides (13) to (17) shown below.

(13): A process for preparing an aromatic halo compound represented by the following formula (21) or a salt or a solvate thereof:

[Formula 11]

(21)

wherein $Y^{20}$ represents a halo group, wherein the halo group is bonded to a carbon atom constituting an element of ring Aa; ring Aa represented by the following formula (24):

[Formula 12]

(24)

represents an aromatic hydrocarbon ring or an aromatic heterocyclic ring (wherein the aromatic hydrocarbon ring and the aromatic heterocyclic ring may each have 1 to 5 identical or different groups as substituents selected from substituent group α'); and substituent group α' represents a group consisting of a halo group, a nitro group, a cyano group, a C1-C8 alkyl group, a halo-C1-C8 alkyl group, a C2-C8 alkenyl group, a C2-C8 alkynyl group, a C6-C14 aryl group, a C4-C10 heteroaryl group, a C3-C8 cycloalkyl group, a C1-C8 alkoxy group, a halo-C1-C8 alkoxy group, a C6-C14 aryloxy group, a C1-C7 acyl group, a C2-C7 acyloxy group, a C1-C8 alkoxycarbonyloxy group, a carboxy group, a C1-C8 alkoxycarbonyl group, a carbamoyl group, a mono- or di-C1-C8 alkylcarbamoyl group, a C1-C7 acylamino group, a C1-C8 alkoxycarbonylamino group, a C1-C8 alkylsulfonylamino group, a C1-C8 alkylthio group, a C1-C8 alkylsulfonyl group, and an oxo group, the process comprising:

[Step 1]:

adding a nitroxide radical compound to an aqueous solution of a hydrohalic acid to prepare a solution, which is then cooled to 10° C. or lower and stirred; and

[Step 2]:

simultaneously adding the following (a) and (b) into the solution of [Step 1] at 10° C. or lower:

(a) an aqueous solution of an aromatic amino compound represented by the following formula (22) or a salt or a solvate thereof:

[Formula 13]

(22)

wherein the amino group is bonded to a carbon atom constituting an element of ring Aa; and ring Aa is as defined above, and (b) an aqueous solution of a diazotization reagent.

(14): A preparation process according to (13), wherein the aromatic hydrocarbon ring or the aromatic heterocyclic ring (wherein the aromatic hydrocarbon ring and the aromatic heterocyclic ring may each have 1 to 5 identical or different groups as substituents selected from substituent group α') as ring Aa represented by the following formula (24):

[Formula 14]

(24)

is a benzene ring, a naphthalene ring, a tetrahydronaphthalene ring, an anthracene ring, a tetrahydroanthracene ring, an octahydroanthracene ring, a phenanthrene ring, a tetrahydrophenanthrene ring, an octahydrophenanthrene ring, a quinoline ring, a dihydroquinoline ring, a tetrahydroquinoline ring, an isoquinoline ring, a dihydroisoquinoline ring, a tetrahydroisoquinoline ring, a quinazoline ring, a dihydroquinazoline ring, a tetrahydroquinazoline ring, a quinoxaline ring, a dihydroquinoxaline ring, a tetrahydroquinoxaline ring, a cinnoline ring, a dihydrocinnoline ring, a tetrahydrocinnoline ring, a phthalazine ring, a dihydrophthalazine ring, a tetrahydrophthalazine ring, a benzotriazine ring, a dihydrobenzotriazine ring, a tetrahydrobenzotriazine ring, an indole ring, an indoline ring, an isoindole ring, an isoindoline ring, a benzoxazole ring, a dihydrobenzoxazole ring, a benzisoxazole ring, a dihydrobenzisoxazole ring, a benzothiazole ring, a dihydrobenzothiazole ring, a benzisothiazole ring, a dihydrobenzisothiazole ring, a benzimidazole ring, a dihydrobenzimidazole ring, a benzopyrazole ring, a dihydrobenzopyrazole ring, a benzotriazole ring, a dihydrobenzotriazole ring, a benzofuran ring, a dihydrobenzofuran ring, a benzothiophene ring, a dihydrobenzothiophene ring, a benzoxadiazole ring, a benzothiadiazole ring, a pyrrole ring, a furan ring, a thiophene ring, an imidazole ring, a pyrazole ring, a triazole ring, a tetrazole ring, an oxazole ring, an isoxazole ring, a triazole ring, an isothiazole ring, an oxadiazole ring, a thiadiazole ring, a pyridine ring, a pyrimidine ring, a pyrazine ring, a pyridazine ring, a triazine ring, a furopyrrole ring, a dihydrofuropyrrole ring, a furothiazole ring, a dihydrofurothiazole ring, a pyranothiazole ring, a dihydropyranothiazole ring, a thienofuran ring, a dihydrothienofuran ring, a thienothiazole ring, a dihydrothienothiazole ring, a pyrrolopyridine ring, a dihydropyrrolopyridine ring, a tetrahydropyrrolopyridine ring, a furopyridine ring, a thienopyridine ring, a dihydrothienopyridine ring, a tetrahydrothienopyridine ring, an oxazolopyridine ring, a dihydrooxazolopyridine ring, a tetrahydrooxazolopyridine ring, an isoxazolopyridine ring, a dihydroisoxazolopyridine ring, a tetrahydroisoxazolopyridine ring, a thiazolopyridine ring, a dihydrothiazolopyridine ring, a tetrahydrothiazolopyridine ring, an isothiazolopyridine ring, a dihydroisothiazolopyridine ring, a tetrahydroisothiazolopyridine ring, an imidazolopyridine ring, a dihydroimidazolopyridine ring, a tetrahydroimidazolopyridine ring, a pyrazolopyridine ring, a dihydropyrazolopyridine ring, a tetrahydropyrazolopyridine ring, a triazolopyridine ring, a dihydrotriazolopyridine ring, a tetrahydrotriazolopyridine ring, a thiazolopyridazine ring, a tetrahydrothiazolopyridazine ring, a pyrrolopyrimidine ring, a dihydropyrrolopyrimidine ring, a naphthyridine ring, a dihydronaphthyridine ring, a tetrahydronaphthyridine ring, a pyridotriazine ring, a dihydropyridotriazine ring, a tetrahydropyridotriazine ring, a pyridopyrazine ring, a dihydropyridopyrazine ring, a tetrahydropyridopyrazine ring, a pyridopyridazine ring, a dihydropyridopyridazine ring, or a tetrahydropyridopyridazine ring; and substituent group α' is the group consisting of a halo group, a nitro group, a cyano group, a C1-C8 alkyl group, a halo-C1-C8 alkyl group, a C2-C8 alkenyl group, a C2-C8 alkynyl group, a C6-C14 aryl group, a C4-C10 heteroaryl group, a C3-C8 cycloalkyl group, a C1-C8 alkoxy group, a halo-C1-C8 alkoxy group, a C6-C14 aryloxy group, a C1-C7 acyl group, a C2-C7 acyloxy group, a C1-C8 alkoxycarbonyloxy group, a carboxy group, a C1-C8 alkoxycarbonyl group, a carbamoyl group, a mono- or di-C1-C8 alkylcarbamoyl group, a C1-C7 acylamino group, a C1-C8 alkoxycarbonylamino group, a C1-C8 alkylsulfonylamino group, a C1-C8 alkylthio group, a C1-C8 alkylsulfonyl group, and an oxo group.

(15): A preparation process according to (13) or (14), wherein the nitroxide radical compound is one or two or more compounds selected from the group consisting of the following:
3-carboxy-2,2,5,5-tetramethyl-1-pyrrolidine 1-oxyl;
3-carbamoyl-2,2,5,5-tetramethylpyrrolidine 1-oxyl;
3-carbamoyl-2,2,5,5-tetramethyl-3-pyrroline 1-oxyl;
4-oxo-2,2,6,6-tetramethylpiperidinoxyl;
4-hydroxy-2,2,6,6-tetramethylpiperidine 1-oxyl;
4-acetamido-2,2,6,6-tetramethylpiperidine 1-oxyl;
2,2,6,6-tetramethylpiperidine 1-oxyl;
3-(maleimidomethyl)-proxyl;
N-(1-oxyl-2,2,6,6-tetramethyl-4-piperidinyl)maleimide; and
1-methyl-2-azaadamantane N-oxyl;
or salts thereof.

(16): A preparation process according to any one of (13) to (15), wherein the amount of the nitroxide radical compound used is stoichiometrically in the range of 0.01 to 0.5 molar equivalents with respect to the reactive substrate organic diazonium salt or organic amino compound or salt or solvate thereof.

(17): A preparation process according to any one of (13) to (16), wherein the diazotization reagent is an alkali metal nitrite or an alkaline earth metal nitrite.

The present invention further provides (18) to (34) shown below.

(18): A process for preparing a compound represented by the following formula (11) or a salt or a solvate thereof:

[Formula 15]

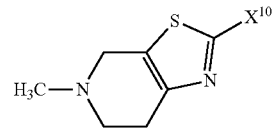

(11)

wherein $X^{10}$ represents a halo group,
the process comprising:
[Step 1]:
adding a nitroxide radical compound to an aqueous solution of a hydrohalic acid to prepare a solution, which is then cooled to 10° C. or lower and stirred; and
[Step 2]:
simultaneously adding the following (a) and (b) into the solution of [Step 1] at 10° C. or lower:
(a) an aqueous solution of a compound represented by the following formula (12) or a salt or a solvate thereof:

[Formula 16]

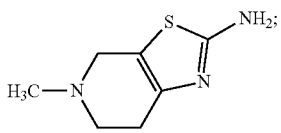

(12)

and
(b) an aqueous solution of a diazotization reagent.

(19): A preparation process according to (18), wherein the halo group is a bromine atom.

(20): A preparation process according to (18) or (19), wherein the compound represented by formula (12) or a salt or a solvate thereof is a hydrobromide of the compound represented by formula (12).

(21): A preparation process according to (20), wherein the hydrobromide of the compound represented by formula (12) is a dihydrobromide compound represented by the following formula (12a) or a hydrate of the salt:

[Formula 17]

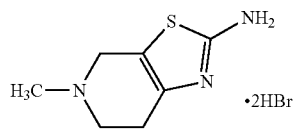

(12a)

(22): A preparation process according to any one of (18) to (21), wherein the diazotization reagent is an alkali metal nitrite or an alkaline earth metal nitrite.

(23): A preparation process according to any one of (18) to (22), wherein the step of simultaneously adding (a) and (b) into the solution of [Step 1] at 10° C. or lower comprises simultaneously adding (a) and (b) in the range of 2 to 10 hours.

(24): A preparation process according to (23), wherein in the simultaneous addition step, the completion time lag between the addition of (a) and the addition of (b) is within 1 hour.

(25): A preparation process according to any one of (18) to (24), wherein [Step 2] is performed under an inert gas atmosphere.

(26): A preparation process according to (25), wherein the inert gas is nitrogen or argon.

(27): A process for preparing a compound represented by the following formula (11b):

[Formula 18]

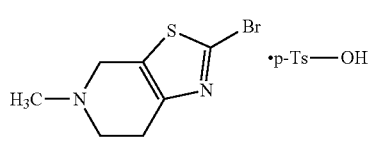

(11b)

the process comprising:

[Step 1]:

adding and dissolving a nitroxide radical compound in an aqueous solution of hydrobromic acid to prepare a solution, which is then cooled to 10° C. or lower and stirred;

[Step 2]:

simultaneously adding the following (a) and (b) into the solution of [Step 1] at 10° C. or lower under a nitrogen or argon gas atmosphere:

(a) an aqueous solution of a compound represented by the following formula (12a) or a hydrate of the salt:

[Formula 19]

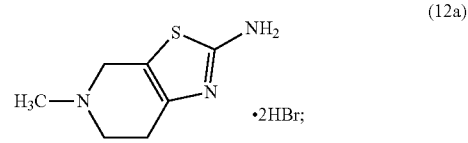

(12a)

and (b) an aqueous solution of an alkali metal nitrite or an alkaline earth metal nitrite; and the step of subsequently neutralizing the resulting compound with an aqueous alkali solution, followed by treatment with p-toluenesulfonic acid to obtain the compound represented by formula (11b).

(28): A process for preparing a compound represented by the following formula (11) or a salt or a solvate thereof according to (18):

[Formula 20]

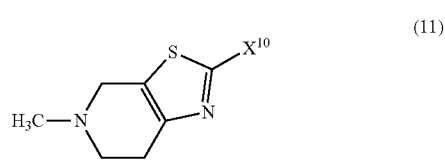

(11)

wherein $X^{10}$ represents a halo group, wherein the compound represented by formula (11) or the salt or the solvate thereof is intended for use as an intermediate for preparation of a compound represented by the following formula (13) or a salt or a solvate thereof:

[Formula 21]

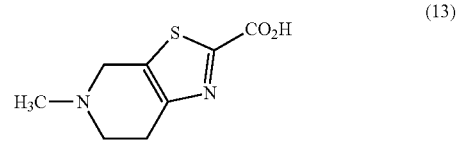

(13)

(29): A process for preparing a compound represented by the following formula (13a):

[Formula 22]

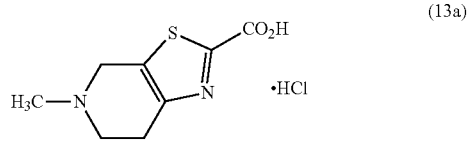

(13a)

the process comprising:

[Step 1]:

adding and dissolving a nitroxide radical compound in an aqueous solution of hydrobromic acid to prepare a solution, which is then cooled to 10° C. or lower and stirred; and

[Step 2]:

simultaneously adding the following (a) and (b) into the solution of [Step 1] at 10° C. or lower under a nitrogen or argon gas atmosphere:

(a) an aqueous solution of a compound represented by the following formula (12a) or a hydrate thereof:

[Formula 23]

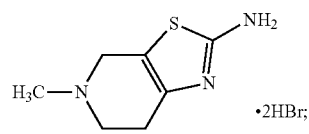

(12a)

·2HBr;

and (b) an aqueous solution of an alkali metal nitrite or an alkaline earth metal nitrite, and further comprising the steps of:

subsequently neutralizing the resulting compound with an aqueous alkali solution, followed by treatment with p-toluenesulfonic acid to obtain a compound represented by the following formula (11a):

[Formula 24]

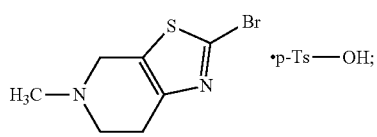

(11a)

·p-Ts—OH;

and neutralizing the compound represented by formula (11a) with alkali, followed by treatment with an alkyl lithium and carbon dioxide and further treatment with hydrochloric acid to obtain the compound represented by formula (13a).

(30): A preparation process according to (29), wherein the alkyl lithium is n-butyl lithium.

(31): A preparation process according to any one of (18) to (30), wherein the nitroxide radical compound is one or two or more compounds selected from the group consisting of the following:

3-carboxy-2,2,5,5-tetramethyl-1-pyrrolidine 1-oxyl;

3-carbamoyl-2,2,5,5-tetramethylpyrrolidine 1-oxyl;

3-carbamoyl-2,2,5,5-tetramethyl-3-pyrroline 1-oxyl;

4-oxo-2,2,6,6-tetramethylpiperidinoxyl;

4-hydroxy-2,2,6,6-tetramethylpiperidine 1-oxyl;

4-acetamido-2,2,6,6-tetramethylpiperidine 1-oxyl;

2,2,6,6-tetramethylpiperidine 1-oxyl;

3-(maleimidomethyl)-proxyl;

N-(1-oxyl-2,2,6,6-tetramethyl-4-piperidinyl)maleimide; and 1-methyl-2-azaadamantane N-oxyl; or salts thereof.

(32): A preparation process according to any one of (18) to (31), wherein the amount of the nitroxide radical compound used is stoichiometrically in the range of 0.01 to 0.5 molar equivalents with respect to compound (12).

(33): A process for preparing a compound represented by the following formula (E-a):

[Formula 25]

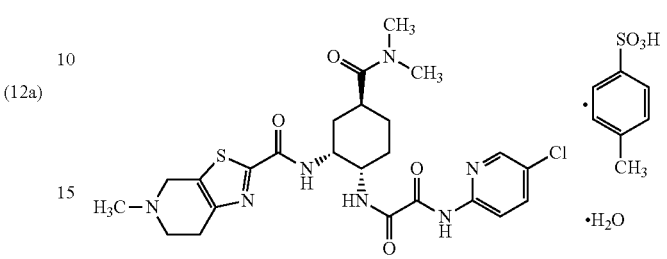

(E-a)

·H$_2$O comprising using compound (13a) prepared using a preparation process according to (29).

(34): A process for preparing a compound represented by the following formula (E-a):

[Formula 26]

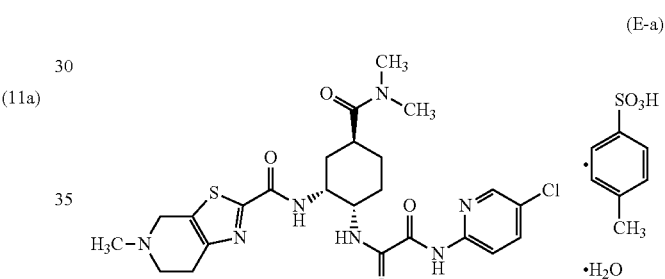

(E-a)

·H$_2$O comprising using compound (13a) prepared using a preparation process according to (29), the process comprising the steps of: deprotecting a Boc group in a compound represented by the following formula (17):

[Formula 27]

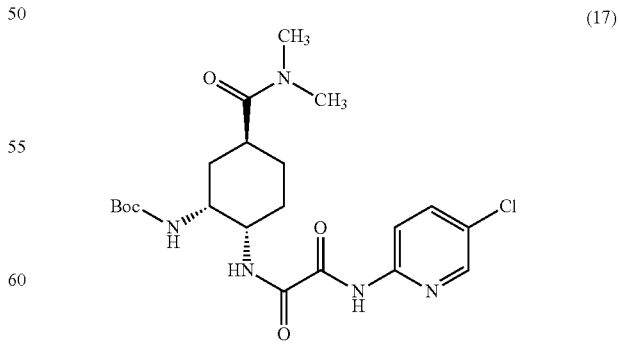

(17)

wherein Boc represents a tert-butoxycarbonyl group, and then condensing the resulting compound with a compound represented by the following formula (13a):

[Formula 28]

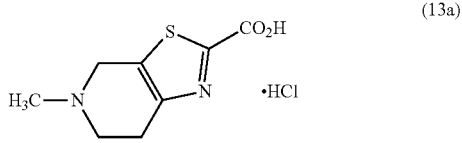

(13a)

in the presence of a base to obtain a compound represented by the following formula (E):

[Formula 29]

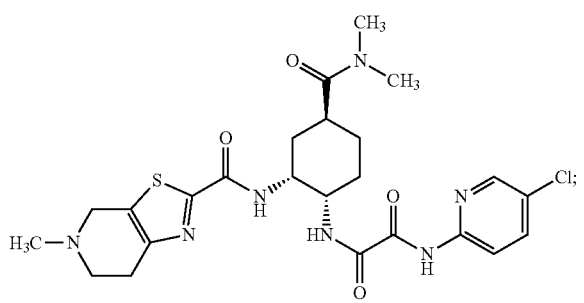

(E)

and treating the compound represented by formula (E) with p-toluenesulfonic acid or a hydrate thereof in aqueous alcohol to obtain the compound represented by formula (E-a).

Advantageous Effects of Invention

The present invention provides a novel method for preparing a substituted aromatic compound such as an aromatic halo compound or a salt thereof from an aromatic amino compound via a transformation reaction of an aromatic diazonium salt using a nitroxide radical compound. The preparation process of the present invention is further suitable for large-scale synthesis and as such, can be applied to an industrial process for preparing an intermediate for pharmaceutical preparation.

DESCRIPTION OF EMBODIMENTS

Hereinafter, the present invention will be described in detail.

An "aromatic compound" according to the present specification refers to a cyclic compound (ring A or ring Aa) represented by the following formula (4) or (24):

[Formula 30]

Ring A and ring Aa mean an aromatic hydrocarbon ring or an aromatic heterocyclic ring. In this context, an "aromatic hydrocarbon ring" compound according to the present invention means a monocyclic or condensed-ring aromatic cyclic hydrocarbon compound. When the aromatic cyclic hydrocarbon compound is a condensed-ring aromatic cyclic compound that is condensed with an additional ring, it can comprise at least one monocyclic aromatic hydrocarbon ring compound that is condensed with one or more additional cyclic compounds selected from the group consisting of an aromatic hydrocarbon ring, an aromatic heterocyclic ring, an aliphatic hydrocarbon ring, and an aliphatic heterocyclic ring. An "aromatic heterocyclic ring compound" according to the present invention means a monocyclic or condensed-ring aromatic heterocyclic compound containing a heteroatom such as a nitrogen, oxygen, or sulfur atom as a constituent of the ring. When the aromatic heterocyclic compound is a condensed-ring aromatic heterocyclic ring compound that is condensed with an additional ring, it can comprise at least one monocyclic aromatic heterocyclic ring compound that is condensed with one or more additional cyclic compounds selected from the group consisting of an aromatic hydrocarbon ring, an aromatic heterocyclic ring, an aliphatic hydrocarbon ring, and an aliphatic heterocyclic ring.

More specifically, an aromatic hydrocarbon ring compound according to the present invention comprises at least one benzene ring as its constituent ring. The benzene ring may be further condensed with one or more cyclic compounds selected from the group consisting of an aromatic hydrocarbon ring, an aromatic heterocyclic ring, an aliphatic hydrocarbon ring, and an aliphatic heterocyclic ring.

Specific examples of a monocyclic or bicyclic aromatic hydrocarbon ring constituting the aromatic hydrocarbon ring compound can include, but are not limited by any means to, a benzene ring, a naphthalene ring, a tetrahydronaphthalene ring, an anthracene ring, a tetrahydroanthracene ring, an octahydroanthracene ring, a phenanthrene ring, a tetrahydrophenanthrene ring, an octahydrophenanthrene ring, a quinoline ring, a dihydroquinoline ring, a tetrahydroquinoline ring, an isoquinoline ring, a dihydroisoquinoline ring, a tetrahydroisoquinoline ring, a quinazoline ring, a dihydroquinazoline ring, a tetrahydroquinazoline ring, a quinoxaline ring, a dihydroquinoxaline ring, a tetrahydroquinoxaline ring, a cinnoline ring, a dihydrocinnoline ring, a tetrahydrocinnoline ring, a phthalazine ring, a dihydrophthalazine ring, a tetrahydrophthalazine ring, a benzotriazine ring, a dihydrobenzotriazine ring, a tetrahydrobenzotriazine ring, an indole ring, an indoline ring, an isoindole ring, an isoindoline ring, a benzoxazole ring, a dihydrobenzoxazole ring, a benzisoxazole ring, a dihydrobenzisoxazole ring, a benzothiazole ring, a dihydrobenzothiazole ring, a benzisothiazole ring, a dihydrobenzisothiazole ring, a benzimidazole ring, a dihydrobenzimidazole ring, a benzopyrazole ring, a dihydrobenzopyrazole ring, a benzotriazole ring, a dihydrobenzotriazole ring, a benzofuran ring, a dihydrobenzofuran ring, a benzothiophene ring, a dihydrobenzothiophene ring, a benzoxadiazole ring, and a benzothiadiazole ring. In this context, the aromatic hydrocarbon rings given the prefix "dihydro", "tetrahydro", or "octahydro" mean condensed-ring compounds whose heterocyclic moiety is hydrogenated. The hydrogenation position may be any position that renders the compound stable. For example, the octahydroanthracene ring includes both of a 1,2,3,4,5,6,7,8-octahydroanthracene ring and a 1,2,3,4,4a,9,9a,10-octahydroanthracene ring. The same holds true for the other condensed-ring compounds. Also, the position of a heterocyclic moiety-constituting heteroatom and the condensation pattern with the benzene ring in condensed-ring compounds having a condensed heterocyclic moiety among the aromatic hydrocarbon rings described above encompass all condensed-ring patterns that render the compound stable. For example, the dihydrobenzothiophene ring includes both a 2,3-dihydrobenzo[b]thiophene ring and a 1,3-dihydrobenzo[c]thiophene ring. The same holds true for the other condensed-ring compounds.

An aromatic heterocyclic ring compound according to the present invention comprises, as its constituent ring, at least one monocyclic aromatic heterocyclic ring that may be further condensed with one or more cyclic compounds selected from the group consisting of an aromatic hydrocarbon ring, an aromatic heterocyclic ring, an aliphatic hydrocarbon ring, and an aliphatic heterocyclic ring. Specific examples of a monocyclic aromatic heterocyclic ring can include, but are not limited by any means to, a pyrrole ring, a furan ring, a thiophene ring, an imidazole ring, a pyrazole ring, a triazole ring, a tetrazole ring, an oxazole ring, an isoxazole ring, a thiazole ring, an isothiazole ring, a pyridine ring, a pyrimidine ring, a pyrazine ring, a pyridazine ring, an oxadiazole ring, a thiadiazole ring, a pyridine ring, a pyrimidine ring, a pyrazine ring, a pyridazine ring, and a triazine ring.

Specific examples of a monocyclic or bicyclic aromatic heterocyclic ring constituting the aromatic heterocyclic ring compound can include, but are not limited by any means to, a pyrrole ring, a furan ring, a thiophene ring, an imidazole ring, a pyrazole ring, a triazole ring, a tetrazole ring, an oxazole ring, an isoxazole ring, a thiazole ring, an isothiazole ring, a triazine ring, an oxadiazole ring, a thiadiazole ring, a pyridine ring, a pyrimidine ring, a pyrazine ring, a pyridazine ring, a triazine ring, a furopyrrole ring, a dihydrofuropyrrole ring, a furothiazole ring, a dihydrofurothiazole ring, a pyranothiazole ring, a dihydropyranothiazole ring, a thienofuran ring, a dihydrothienofuran ring, a thienothiazole ring, a dihydrothienothiazole ring, an indole ring, a dihydroindole ring, a tetrahydroindole ring, an isoindole ring, a dihydroisoindole ring, a tetrahydroisoindole ring, a benzoxazole ring, a dihydrobenzoxazole ring, a tetrahydrobenzoxazole ring, a benzisoxazole ring, a dihydrobenzisoxazole ring, a tetrahydrobenzisoxazole ring, a benzothiazole ring, a dihydrobenzothiazole ring, a tetrahydrobenzothiazole ring, a benzisothiazole ring, a dihydrobenzisothiazole ring, a tetrahydrobenzisothiazole ring, a benzimidazole ring, a dihydrobenzimidazole ring, a tetrahydrobenzimidazole ring, a benzopyrazole ring, a dihydrobenzopyrazole ring, a tetrahydrobenzopyrazole ring, a benzotriazole ring, a dihydrobenzotriazole ring, a tetrahydrobenzotriazole ring, a benzofuran ring, a dihydrobenzofuran ring, a tetrahydrobenzofuran ring, a benzothiophene ring, a dihydrobenzothiophene ring, a tetrahydrobenzothiophene ring, a pyrrolopyridine ring, a dihydropyrrolopyridine ring, a tetrahydropyrrolopyridine ring, a furopyridine ring, a thienopyridine ring, a dihydrothienopyridine ring, a tetrahydrothienopyridine ring, an oxazolopyridine ring, a dihydrooxazolopyridine ring, a tetrahydrooxazolopyridine ring, an isoxazolopyridine ring, a dihydroisoxazolopyridine ring, a tetrahydroisoxazolopyridine ring, a thiazolopyridine ring, a dihydrothiazolopyridine ring, a tetrahydrothiazolopyridine ring, an isothiazolopyridine ring, a dihydroisothiazolopyridine ring, a tetrahydroisothiazolopyridine ring, an imidazolopyridine ring, a dihydroimidazolopyridine ring, a tetrahydroimidazolopyridine ring, a pyrazolopyridine ring, a dihydropyrazolopyridine ring, a tetrahydropyrazolopyridine ring, a triazolopyridine ring, a dihydrotriazolopyridine ring, a tetrahydrotriazolopyridine ring, a thiazolopyridazine ring, a tetrahydrothiazolopyridazine ring, a pyrrolopyrimidine ring, a dihydropyrrolopyrimidine ring, a naphthyridine ring, a dihydronaphthyridine ring, a tetrahydronaphthyridine ring, a pyridotriazine ring, a dihydropyridotriazine ring, a tetrahydropyridotriazine ring, a pyridopyrazine ring, a dihydropyridopyrazine ring, a tetrahydropyridopyrazine ring, a pyridopyridazine ring, a dihydropyridopyridazine ring, a tetrahydropyridopyridazine ring, a quinoline ring, a dihydroquinoline ring, a tetrahydroquinoline ring, an isoquinoline ring, a dihydroisoquinoline ring, a tetrahydroisoquinoline ring, a quinazoline ring, a dihydroquinazoline ring, a tetrahydroquinazoline ring, a quinoxaline ring, a dihydroquinoxaline ring, a tetrahydroquinoxaline ring, a cinnoline ring, a dihydrocinnoline ring, a tetrahydrocinnoline ring, a phthalazine ring, a dihydrophthalazine ring, a tetrahydrophthalazine ring, a benzotriazine ring, a dihydrobenzotriazine ring, and a tetrahydrobenzotriazine ring.

In this context, the aromatic heterocyclic rings given the prefix "dihydro" or "tetrahydro" mean condensed-ring compounds whose condensed-ring moiety other than the one monocyclic aromatic heterocyclic ring moiety is hydrogenated. The hydrogenation position may be any position that renders the compound stable. Also, the position of a heterocyclic moiety-constituting heteroatom and the condensation pattern with an additional ring in condensed-ring compounds among the aromatic heterocyclic rings described above encompass all condensed-ring patterns that render the compound stable. Taking the thiazolopyridyl group according to the present invention as an example, it encompasses thiazolopyridyl groups having any of the condensed-ring patterns of a thiazolo[4,5-b]pyridine ring, a thiazolo[4,5-c]pyridine ring, a thiazolo[5,4-b]pyridine ring, and a thiazolo[5,4-c]pyridine ring. The tetrahydrothiazolopyridine ring encompasses all of the 4,5,6,7-tetrahydro forms of these thiazolopyridyl rings. The same holds true for the other condensed-ring compounds.

In the present specification, among the aromatic hydrocarbon rings and the aromatic heterocyclic rings exemplified as above, condensed-ring aromatic hydrocarbon ring or aromatic heterocyclic ring compounds having two or more rings can contain an aromatic hydrocarbon ring or an aromatic heterocyclic ring as at least one ring. This means that substituent Y or $NH_2$ (amino group) in the compounds of formulae (1) and (2) is positioned on the aromatic hydrocarbon ring or the aromatic heterocyclic ring.

Ring A and ring Aa according to the present specification are each preferably a benzene ring, a naphthalene ring, a tetrahydronaphthalene ring, an anthracene ring, a tetrahydroanthracene ring, an octahydroanthracene ring, a phenanthrene ring, a tetrahydrophenanthrene ring, an octahydrophenanthrene ring, a quinoline ring, a dihydroquinoline ring, a tetrahydroquinoline ring, an isoquinoline ring, a dihydroisoquinoline ring, a tetrahydroisoquinoline ring, a quinazoline ring, a dihydroquinazoline ring, a tetrahydroquinazoline ring, a quinoxaline ring, a dihydroquinoxaline ring, a tetrahydroquinoxaline ring, a cinnoline ring, a dihydrocinnoline ring, a tetrahydrocinnoline ring, a phthalazine ring, a dihydrophthalazine ring, a tetrahydrophthalazine ring, a benzotriazine ring, a dihydrobenzotriazine ring, a tetrahydrobenzotriazine ring, an indole ring, an indoline ring, an isoindole ring, an isoindoline ring, a benzoxazole ring, a dihydrobenzoxazole ring, a benzisoxazole ring, a dihydrobenzisoxazole ring, a benzothiazole ring, a dihydrobenzothiazole ring, a benzisothiazole ring, a dihydrobenzisothiazole ring, a benzimidazole ring, a dihydrobenzimidazole ring, a benzopyrazole ring, a dihydrobenzopyrazole ring, a benzotriazole ring, a dihydrobenzotriazole ring, a benzofuran ring, a dihydrobenzofuran ring, a benzothiophene ring, a dihydrobenzothiophene ring, a benzoxadiazole ring, a benzothiadiazole ring, a pyrrole ring, a furan ring, a thiophene ring, an imidazole ring, a pyrazole ring, a triazole ring, a tetrazole ring, an oxazole ring, an isoxazole ring, a thiazole ring, an isothiazole ring, an oxadiazole ring, a thiadiazole ring, a pyridine ring, a pyrimidine ring, a pyrazine ring, a pyridazine ring, a triazine ring, a furopyrrole ring, a dihydrofuropyrrole ring, a furothiazole ring, a dihydrofurothiazole ring, a pyranothiazole ring, a dihydropyranothiazole ring, a thienofuran ring, a dihydrothienofuran ring, a thienothiazole ring, a dihydrothienothiazole ring, a pyrrolopyridine ring, a dihydropyrrolopyridine ring, a tetrahydropyrrolopyridine ring, a furopyridine ring, a thienopyridine ring, a dihydrothienopyridine ring, a tetrahydrothienopyridine ring, an oxazolopyridine ring, a dihydrooxazolopyridine ring, a tetrahydrooxazolopyridine ring, an isoxazolopyridine ring, a dihydroisoxazolopyridine ring, a tetrahydroisoxazolopyridine ring, a triazolopyridine ring, a dihydrothiazolopyridine ring, a tetrahydrothiazolopyridine ring, an isothiazolopyridine ring, a dihydroisothiazolopyridine ring, a tetrahydroisothiazolopyridine ring, an imidazolopyridine ring, a dihydroimidazolopyridine ring, a tetrahydroimidazolopyridine ring, a pyrazolopyridine ring, a dihydropyrazolopyridine ring, a tetrahydropyrazolopyridine ring, a triazolopyridine ring, a dihydrotriazolopyridine ring, a tetrahydrotriazolopyridine ring, a thiazolopyridazine ring, a tetrahydrothiazolopyridazine ring, a pyrrolopyrimidine ring, a dihydropyrrolopyrimidine ring, a naphthyridine ring, a dihydronaphthyridine ring, a tetrahydronaphthyridine ring, a pyridotriazine ring, a dihydropyridotriazine ring, a tetrahydropyridotriazine ring, a pyridopyrazine ring, a dihydropyridopyrazine ring, a tetrahydropyridopyrazine ring, a pyridopyridazine ring, a dihydropyridopyridazine ring, or a tetrahydropyridopyridazine ring.

An "aromatic compound" according to the present specification refers to a cyclic compound (ring A or ring Aa) represented by formula (4) or (24). Ring A and ring Aa means an aromatic hydrocarbon ring or an aromatic heterocyclic ring. The aromatic hydrocarbon ring and the aromatic heterocyclic ring may each have 1 to 5 identical or different groups as substituents selected from substituent group α or substituent group α'. Hereinafter, substituents that may be added to the aromatic hydrocarbon ring and the aromatic heterocyclic ring will be described.

In an aromatic compound represented by the following formula (4a) or (24a):

[Formula 31]

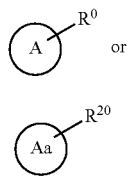

1 to 5 hydrogen atoms on the aromatic ring may be replaced by a substituent $R^0$ or $R^{20}$ that does not inhibit the reaction of the present invention. The substituents "$R^0$ and $R^{20}$" each mean 1 to 5 identical or different substituents. The substituents $R^0$ and $R^{20}$ can be any organic group without limitations to its type as long as the reaction of the present invention is not inhibited. In this context, an organic group means, for example, a monovalent group composed of a carbon atom, a hydrogen atom, a nitrogen atom, an oxygen atom, a sulfur atom, a halo atom, phosphorus, and silicon, etc., or a divalent oxo group.

Preferred examples of the substituents "$R^0$ and $R^{20}$" can specifically include, but are not particularly limited to, 1 to 5 groups selected from the group consisting of a halo group, a nitro group, a cyano group, a C1-C8 alkyl group, a halo-C1-C8 alkyl group, a C2-C8 alkenyl group, a C2-C8 alkynyl group, a C6-C14 aryl group, a C4-C10 heteroaryl group, a C3-C8 cycloalkyl group, a C1-C8 alkoxy group, a halo-C1-C8 alkoxy group, a C2-C8 alkenyloxy group, a C4-C14 aryloxy group, a C1-C7 acyl group, a C2-C7 acyloxy group, a C1-C8 alkoxycarbonyloxy group, a carboxy group, a C1-C8 alkoxycarbonyl group, a carbamoyl group, a mono- or di-C1-C8 alkylcarbamoyl group, a C1-C7 acylamino group, a C1-C8 alkoxycarbonylamino group, a C1-C8 alkylsulfonylamino group, a C1-C8 alkylthio group, a C1-C8 alkylsulfonyl group, and an oxo group.

A halo group according to the present specification means a fluoro, chloro, bromo, or iodo group and is preferably a chloro or bromo group.

A C1-C8 alkyl group refers to a monovalent linear or branched hydrocarbon group having 1 to 8 carbon atoms. Examples thereof can include methyl, ethyl, n-propyl, isopropyl (2-propyl), n-butyl, tert-butyl, 1-methylpropyl, 2-methylpropyl, 3-methylpropyl, n-pentyl, 1-methylbutyl, 2-methylbutyl, 3-methylbutyl, 1,1-dimethylpropyl, 1,2-dimethylpropyl, 2,2-dimethylpropyl, 2-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 1,4-dimethylbutyl, 2,3-dimethylbutyl, 2,4-dimethylbutyl, 3,4-dimethylbutyl, 2-ethylbutyl, n-heptyl, 1-methylhexyl, 2-methylhexyl, 3-methylhexyl, 4-methylhexyl, 5-methylhexyl, 1,1-dimethylpentyl, 2,2-dimethylpentyl, 3,3-dimethylpentyl, 4,4-dimethylpentyl, 1,2-dimethylpentyl, 1,3-dimethylpentyl, 1,4-dimethylpentyl, 2,3-dimethylpentyl, 2,4-dimethylpentyl, 3,4-dimethylpentyl, 1-ethylpentyl, 2-ethylpentyl, 3-ethylpentyl, 1-propylbutyl, 2,2-diethylpropyl, n-octyl, 1-methylheptyl, 2-methylheptyl, 3-methylheptyl, 4-methylheptyl, 5-methylheptyl, 6-methylheptyl, 1,1-dimethylhexyl, 2,2-dimethylhexyl, 3,3-dimethylhexyl, 4,4-dimethylhexyl, 5,5-dimethylhexyl, 1,2-dimethylhexyl, 1,3-dimethylhexyl, 1,4-dimethylhexyl, 1,5-dimethylhexyl, 2,3-dimethylhexyl, 2,4-dimethylhexyl, 2,5-dimethylhexyl, 3,4-dimethylhexyl, 3,5-dimethylhexyl, 4,5-dimethylhexyl, 1-ethylhexyl, 2-ethylhexyl, 3-ethylhexyl, 4-ethylhexyl, 1,1,2-trimethylpentyl, 1,2,2-trimethylpentyl, 1,2,3-trimethylpentyl, 1,3,3-trimethylpentyl, 1,3,4-trimethylpentyl, 1,4,4-trimethylpentyl, 2,2,3-trimethylpentyl, 2,3,3-trimethylpentyl, 2,3,4-trimethylpentyl, 2,4,5-trimethylpentyl, 1-ethyl-1-methylpentyl, 1-ethyl-2-methylpentyl, 1-ethyl-3-methylpentyl, 1-ethyl-4-methylpentyl, 2-ethyl-1-methylpentyl, 2-ethyl-2-methylpentyl, 2-ethyl-3-methylpentyl, 2-ethyl-4-methylpentyl, 3-ethyl-1-methylpentyl, 3-ethyl-2-methylpentyl, 3-ethyl-3-methylpentyl, 3-ethyl-4-methylpentyl, 1,1-diethylbutyl, 1,2-diethylbutyl, 2,2-diethylbutyl, 1-methyl-2-propylbutyl, 2-methyl-1-propylbutyl, 3-methyl-1-propylbutyl, and 1,1-diethyl-2-methylpropyl groups.

A halo-C1-C8 alkyl group according to the present specification means a C1-C8 alkyl group having 1 to 5 identical or different halo groups. Examples thereof can include fluoromethyl, chloromethyl, difluoromethyl, trifluoromethyl, trichloromethyl, 2,2,2-trifluoroethyl, 2,2,2-trichloroethyl, and 1,1,2,2,2-pentafluoroethyl groups.

A C2-C8 alkenyl group refers to a linear or branched unsaturated hydrocarbon having 2 to 8 carbon atoms and at least one or more double bonds. Examples thereof can include ethenyl, prop-1-enyl, but-1-enyl, buta-1,3-dienyl, pent-1-enyl, hex-1-enyl, hept-1-enyl, and oct-1-enyl groups.

A C2-C8 alkynyl group refers to a linear or branched unsaturated hydrocarbon having 2 to 8 carbon atoms and at least one or more double bonds. Examples thereof can include ethynyl, prop-1-ynyl, but-1-ynyl, buta-1,3-diynyl, pent-1-ynyl, hex-1-ynyl, hept-1-ynyl, and oct-1-ynyl groups.

Examples of a C6-C14 aryl group can include phenyl and naphthyl groups. Examples of a C4-C10 heteroaryl group can include pyrrolyl, thienyl, furyl, pyridyl, pyrimidinyl, pyrazinyl, and pyridazinyl groups. Examples of a C4-C14 aryloxy group can include pyrrolyloxy, pyridyloxy, pyrimidinyloxy, pyrazinyloxy, pyridazinyloxy, phenyloxy, and naphthyloxy groups.

Examples of a C1-C7 acyl group can include formyl, acetyl, propionyl, cyclopropanoyl, butyryl, cyclobutanoyl, pentanoyl, cyclopentanoyl, hexanoyl, cyclohexanoyl, and benzoyl groups.

A C3-C8 cycloalkyl group refers to a monovalent group composed of a saturated hydrocarbon ring having 3 to 8 carbon atoms. Examples thereof can include cyclopropyl, cyclobutyl, cyclopentyl, cyclohexyl, cycloheptyl, and cyclooctyl groups.

A C1-C8 alkoxy group refers to a C1-C8 alkyloxy group composed of an alkyl group having 1 to 8 carbon atoms and an oxygen atom. Examples thereof can include methoxy, ethoxy, n-propoxy, isopropoxy, n-butoxy, isobutyloxy, n-pentyloxy, n-hexyloxy, n-heptyloxy, and n-octyloxy groups.

Examples of a C2-C7 acyloxy group can include acetyloxy, propionyloxy, butyryloxy, pentanoyloxy, hexanoyloxy, heptanoyloxy, and octanoyloxy groups.

A halo-C1-C8 alkoxy group means a C1-C8 alkoxy group having 1 to 5 identical or different halo groups. Examples thereof can include fluoromethoxy, chloromethoxy, difluoromethoxy, trifluoromethoxy, 2,2,2-trifluoroethoxy, 2,2,2-trichloroethoxy, 2,2,2-trichloroethoxy, and 1,1,2,2,2-pentafluoroethoxy groups.

A C2-C8 alkenyloxy group refers to a C2-C8 alkenyloxy group composed of an alkenyl group having 2 to 8 carbon atoms and an oxygen atom. Examples thereof can include allyloxy, but-3-enyloxy, and, pent-4-enyloxy groups.

Examples of a C1-C8 alkoxycarbonyl group can include methoxycarbonyl, ethoxycarbonyl, propoxycarbonyl, butoxycarbonyl, pentyloxycarbonyl, hexyloxycarbonyl, heptyloxycarbonyl, and octyloxycarbonyl groups.

A C1-C8 alkoxycarbonyloxy group refers to a group composed of a C1-C8 alkoxycarbonyl group and an oxygen atom. Examples thereof can include methoxycarbonyloxy and ethoxycarbonyloxy groups.

A mono- or di-C1-C8 alkylcarbamoyl group refers to a carbamoyl group whose nitrogen atom is substituted by one C1-C8 alkyl group or two identical or different C1-C8 alkyl groups. Examples of a mono-C1-C8 alkylcarbamoyl group can include N-methylcarbamoyl and N-ethylcarbamoyl groups.

Examples of a di-C1-C8 alkylcarbamoyl group can include N,N-dimethylcarbamoyl, N,N-diethylcarbamoyl, and N-ethyl-N-methylcarbamoyl groups.

Examples of a C1-C7 acylamino group can include formylamino, acetylamino, propionylamino, (cyclopropionyl) amino, butyrylamino, pentanoylamino, hexanoylamino, and benzoylamino groups.

A C1-C8 alkoxycarbonylamino group refers to a group composed of a C1-C8 alkoxycarbonyl group and an amino group. Examples thereof can include methoxycarbonylamino, ethoxycarbonylamino, and propoxycarbonylamino groups.

A C1-C8 alkyl group, a C2-C8 alkenyl group, or the like may have an optical isomer based on an asymmetric carbon or a geometric isomer based on a substituent bonded to the double bond. The present specification encompasses all of these isomers.

A cyclic compound (ring A or ring Aa) represented by formula (4) or (24) may not have a substituent "$R^0$ or $R^{20}$" on the aromatic ring. When the cyclic compound has the substituent "$R^0$ or $R^{20}$", "$R^0$ or $R^{20}$" is preferably 1 to 5 identical or different groups selected from the group consisting of a halo group, a nitro group, a C1-C8 alkyl group, and a C1-C8 alkoxy group.

An "aromatic diazonium salt" according to the present specification is represented by the following formula (3):

[Formula 32]

(3)

wherein ring A is as defined above; and the diazonio group (diazonium group) is bonded to a carbon atom constituting an element of ring A, and is obtained "in situ" by treating an "aromatic amino compound" represented by the following formula (2):

[Formula 33]

(2)

wherein the amino group is bonded to a carbon atom constituting an element of ring A; and ring A is as defined above, with a diazotization reagent in the presence of an acid such as hydrochloric acid or sulfuric acid in a solvent. An aromatic diazonium compound usually forms a salt. The "aromatic diazonium salt" means a salt formed by an anion (counter ion) ($X^-$) by the removal of a proton ($H^+$) from a Bronsted acid (HX). The salt is preferably, for example, chloride, bromide, sulfate, nitrate, perchlorate, tetrafluoroborate, or hexafluorophosphate.

In this context, examples of the Bronsted acid (HX) can include sulfuric acid ($H_2SO_4$), nitric acid ($HNO_3$), hydrochloric acid (HCl), bromic acid (HBr), iodic acid (HI), perchloric acid ($HClO_4$), tetrafluoroboric acid ($HBF_4$), and hexafluorophosphoric acid ($HPF_4$). These Bronsted acids may be used in the form of an alkali metal salt, an alkaline earth metal salt, a palladium salt, a silver salt, a cadmium salt, or the like.

A "transformation reaction" of an aromatic diazonium salt according to the present specification is a reaction by which the diazonio group (diazonium group) in formula (3) is eliminated to form a substituted aromatic compound represented by the following formula (1) or (21) having a halo group, a cyano group, a sulfo group, a hydroxy group, a nitro group, a hydrogen atom, or an aryloxy group as a "substituent" substituted therefor:

[Formula 34]

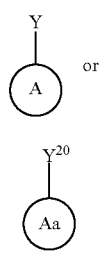

(1)

(21)

wherein substituent Y represents a substituent substituted in situ for the diazonio group and is bonded to a carbon atom constituting an element of ring A; or $Y^{20}$ represents a halo group; and ring A and ring Aa are as defined above.

A "substituted aromatic compound" according to the present specification means a compound derived from an aromatic diazonium compound (salt) by the in situ replacement of the diazonio group (diazonium group) by a halo group, a cyano group, a sulfo group, a hydroxy group, a nitro group, a hydrogen atom, or an aryloxy group as the "substituent" and specifically refers to an aromatic halo compound, an aromatic cyano compound, an aromatic sulfo compound, an aromatic hydroxy compound, an aromatic nitro compound, an aromatic hydrogenated compound, and an aromatic aryloxy compound.

Examples of the "source material for the substituent" according to the present specification can include hydrogen halide, alkali metal halide, hydrogen cyanide, sodium cyanide, potassium cyanide, sulfuric acid, potassium sulfite, sodium sulfite, sodium bisulfate, sodium nitrite, potassium nitrite, hypophosphorous acid, and a hydroxyaryl derivative. The desired "source material for the substituent" can be selected to thereby prepare the desired "substituted aromatic compound". Examples of the "substituent" according to the present specification can include a halo group, a cyano group, a sulfo group, a hydroxy group, a nitro group, a hydrogen atom, and an aryloxy group. Specific examples of a "substituted aromatic compound" can include an aromatic halo compound, an aromatic cyano compound, an aromatic sulfo compound, an aromatic hydroxy compound, an aromatic nitro compound, an aromatic hydrogenated compound, and an aromatic aryloxy compound.

An aromatic diazonium salt according to the present specification can be prepared by treating an aromatic amino compound or a salt thereof with a diazotization reagent. Examples of the diazotization reagent can include nitrous acid, alkali metal nitrite, and C1-C8 alkyl ester of nitrous acid. The alkali metal nitrite is preferably sodium nitrite or potassium nitrite. The C1-C8 alkyl ester of nitrous acid is preferably nitrous acid ethyl ester, nitrous acid n-propyl ester, nitrous acid isopropyl ester, nitrous acid n-butyl ester, nitrous acid isobutyl ester, nitrous acid t-butyl ester, nitrous acid isoamyl ester, or the like.

A nitroxide radical compound according to the present specification may form a salt of the nitroxide radical compound or may form a solvate of the nitroxide radical compound or a solvate of the salt of the nitroxide radical compound as long as the reaction of the present specification is not inhibited.

Examples of a nitroxide radical compound according to the present specification can include a compound represented by the following formula (5) or a salt thereof:

[Formula 35]

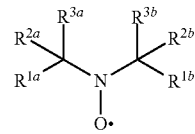

(5)

wherein $R^{1a}$ and $R^{1b}$ are identical or different and each represent a hydrogen atom, a methyl group, or an ethyl group; $R^{2a}$ and $R^{2b}$ 1) are identical or different and each represent a hydrogen atom, a methyl group, or an ethyl group, or 2) together form a 2-azaadamantyl ring with $R^{3a}$ and $R^{3b}$, the carbon atoms bonded to $R^{2a}$, $R^{2b}$, $R^{3a}$, and $R^{3b}$, and the nitrogen atom; and $R^{3a}$ and $R^{3b}$ 3) are identical or different and each represent a hydrogen atom, a methyl group, or an ethyl group, 4) together form a dimethylene group or a trimethylene group [wherein the dimethylene or trimethylene group may have one group as a substituent selected from the group consisting of a C1-C3 alkyl group, a hydroxy group, a C1-C3 alkoxy group, a phosphonooxy group, a benzyloxy group, a phenoxy group, a nitro group, a cyano group, a carboxy group, a C1-C3 alkoxycarbonyl group, a carbamoyl group, a N-mono-(C1-C3 alkyl)carbamoyl group, a N,N-di-(C1-C3 alkyl)carbamoyl group, an amino group, a (C2-C5 alkanoyl)amino group, a benzoylamino group, a 2,5-di-oxo-pyrrolidin-1-yl group, a 2,5-dioxo-2,5-dihydropyrrol-1-yl group, a (2,5-dioxo-2,5-dihydropyrrol-1-yl)methyl group, an oxo group, and a hydroxyimino group], or 5) together form an ethene-1,2-diyl group (wherein the ethene-1,2-diyl group may have one group as a substituent selected from the group consisting of a C1-C3 alkyl group, a hydroxy-C1-C3 alkyl group, a carboxy group, and a carbamoyl group).

In this context, a 2-azaadamantyl ring formed by $R^{2a}$ and $R^{2b}$ together with $R^{3a}$ and $R^{3b}$, the carbon atoms bonded to $R^{2a}$, $R^{2b}$, $R^{3a}$, and $R^{3b}$, and the nitrogen atom 2) means a compound represented by the following formula (5a):

[Formula 36]

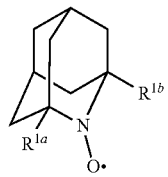

(5a)

A compound wherein 4) $R^{3a}$ and $R^{3b}$ together form a dimethylene group or a trimethylene group means a compound represented by the following formula (5b-1) or (5b-2):

[Formula 37]

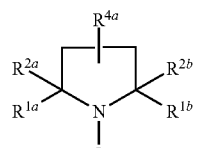
(5b-1)

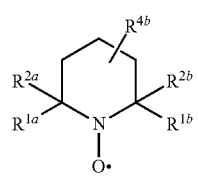
(5b-2)

wherein $R^{4a}$ and $R^{4b}$ each independently represent a hydrogen atom or may be one group as a substituent selected from the group consisting of a C1-C3 alkyl group, a hydroxy group, a C1-C3 alkoxy group, a phosphonooxy group, a benzyloxy group, a phenoxy group, a nitro group, a cyano group, a carboxy group, a C1-C3-alkoxycarbonyl group, a carbamoyl group, a N-mono-(C1-C3 alkyl)carbamoyl group, a N,N-di-(C1-C3 alkyl)carbamoyl group, an amino group, a (C2-C5 alkanoyl)amino group, a benzoylamino group, a 2,5-dioxo-pyrrolidin-1-yl group, a 2,5-dioxo-2,5-dihydropyrrol-1-yl group, a (2,5-dioxo-2,5-dihydropyrrol-1-yl)methyl group, an oxo group, and a hydroxyimino group.

A compound wherein 4) $R^{3a}$ and $R^{3b}$ together form an ethene-1,2-diyl group means a compound represented by the following formula (5c):

[Formula 38]

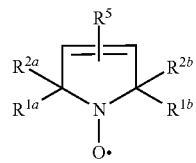
(5c)

wherein $R^5$ may be one group as a substituent selected from the group consisting of a C1-C3 alkyl group, a hydroxy-C1-C3 alkyl group, a carboxy group, and a carbamoyl group.

In this context, $R^{1a}$ and $R^{1b}$ in compound (5) are identical or different and are each preferably a hydrogen atom or a methyl group.

$R^{2a}$ and $R^{2b}$ in compound (5) are identical or different and are each preferably a hydrogen atom or a methyl group.

$R^{3a}$ and $R^{3b}$ in compound (5) are identical or different and are each preferably a hydrogen atom or a methyl group.

Alternatively, $R^{3a}$ and $R^{3b}$ in compound (5) are preferably the following 4) or 5):

4) a dimethylene group or a trimethylene group formed by $R^{3a}$ and $R^{3b}$ together, wherein a compound having a dimethylene group or a trimethylene group formed by $R^{3a}$ and $R^{3b}$ together is represented by formula (5b-1) or (5b-2); and 5) an ethene-1,2-diyl group formed by $R^{3a}$ and $R^{3b}$ together, wherein a compound having the ethene-1,2-diyl group is represented by formula (5c).

$R^{4a}$ and $R^{4b}$ in formulae (5b-1) and (5b-2) each independently represent a hydrogen atom or are each preferably one group as a substituent selected from the group consisting of a hydroxy group, a C1-C3 alkoxy group, a benzyloxy group, a carboxy group, a carbamoyl group, a N-mono-(C1-C3 alkyl) carbamoyl group, a N,N-di-(C1-C3 alkyl)carbamoyl group, an acetylamino group, a benzoylamino group, a 2,5-dioxo-pyrrolidin-1-yl group, and a 2,5-dioxo-2,5-dihydropyrrol-1-yl group.

A nitroxide radical compound according to the present specification is preferably one or two or more compounds selected from the group consisting of the following:

3-carboxy-2,2,5,5-tetramethyl-1-pyrrolidine 1-oxyl (5d);
3-carbamoyl-2,2,5,5-tetramethylpyrrolidine 1-oxyl (5e);
3-carbamoyl-2,2,5,5-tetramethyl-3-pyrroline 1-oxyl (5f);
4-oxo-2,2,6,6-tetramethylpiperidinoxyl (5g);
4-hydroxy-2,2,6,6-tetramethylpiperidine 1-oxyl (5h);
4-acetamido-2,2,6,6-tetramethylpiperidine 1-oxyl (5I);
2,2,6,6-tetramethylpiperidine 1-oxyl (5j);
3-(maleimidomethyl)-proxyl (5k);
N-(1-oxyl-2,2,6,6-tetramethyl-4-piperidinyl)maleimide (5l); and
1-methyl-2-azaadamantane N-oxyl (5m); or salts thereof.

Compounds (5d) to (5m) have chemical structures of the following formulae:

[Formula 39]

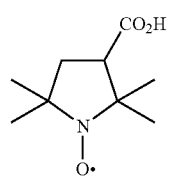
(5d)

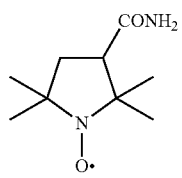
(5e)

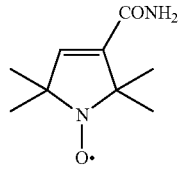
(5f)

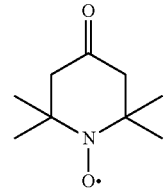
(5g)

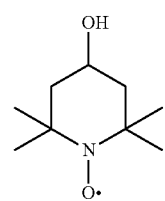
(5h)

(5i)

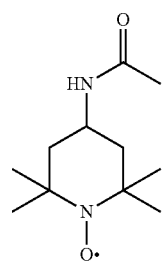

(5j)

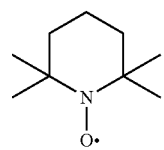

(5k)

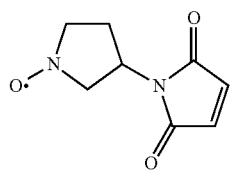

(5l)

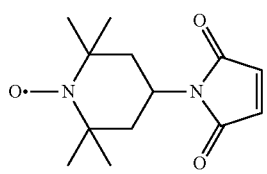

(5m)

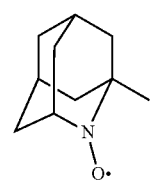

It is particularly preferred that the nitroxide radical compound according to the present specification is 4-hydroxy-2,2,6,6-tetramethylpiperidine 1-oxyl (5h); or 2,2,6,6-tetramethylpiperidine 1-oxyl (5j).

Hereinafter, the preparation process of the present invention will be described in detail.

The preparation process of the present application using benzene as an aromatic compound will be described in [Scheme 1] below as an exemplary embodiment of the present invention.

[Scheme 1]

[Formula 40]

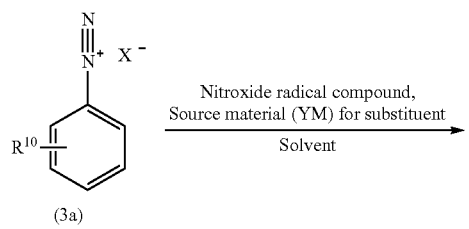

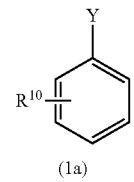

(1a)

wherein the nitroxide radical compound is as defined above; $X^-$ represents $HSO_4^-$, $NO_3^-$, $Cl^-$, $Br^-$, $I^-$, $ClO_4^-$, $BF_4^-$, or $PF_6^-$; the source material "YM" for the substituent represents hydrogen halide, alkali metal halide, hydrogen cyanide, sodium cyanide, potassium cyanide, sulfuric acid, potassium sulfite, sodium sulfite, sodium bisulfate, sodium nitrite, potassium nitrite, hypophosphorous acid, or a hydroxyaryl derivative; Y represents a halo group, a cyano group, a sulfo group, a hydroxy group, a nitro group, a hydrogen atom, or an aryloxy group; and $R^{10}$ represents a hydrogen atom or represents one or more identical or different organic groups as substituents on the benzene ring, wherein the substituents are not particularly limited by their types as long as the reaction is not inhibited.

The following [Scheme 1a] represents a process for preparing bromobenzene as a specific example of [Scheme 1]:

[Scheme 1a]

[Formula 41]

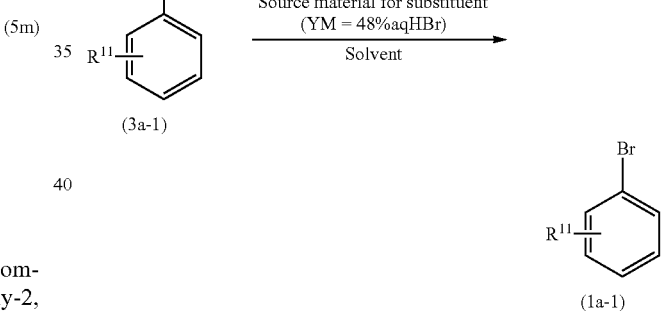

wherein the nitroxide radical compound and $X^-$ are as defined above; $R^{11}$ represents a hydrogen atom or represents one or more identical or different organic groups as substituents on the benzene ring, wherein the substituents are not particularly limited by their types as long as the reaction is not inhibited.

Diazonium salt (3a-1) can be treated with the nitroxide radical compound in the presence of 48% hydrobromic acid in a solvent to prepare bromobenzene (1a-1).

The solvent is not particularly limited as long as the reaction is not inhibited. Water, alcohol solvents, the polar solvent dimethyl sulfoxide, and nitrile solvents such as acetonitrile are preferably used alone or as a mixed solvent. Water, an aqueous alcohol solvent, and/or aqueous acetonitrile are particularly preferred. The amount of the solvent used is not particularly limited and is preferably 8 to 50 parts by volume (V/W), more preferably 10 to 20 parts by volume (V/W), with respect to 1 part of compound (3a-1).

The amount of the 48% hydrobromic acid used is stoichiometrically preferably 2 to 10 molar equivalents, more preferably 3 to 5 molar equivalents, with respect to compound (1a-1).

The nitroxide radical compound used is preferably any of those described above and is preferably 4-hydroxy-2,2,6,6-tetramethylpiperidine 1-oxyl (5h) (TEMPOL) or 2,2,6,6-tetramethylpiperidine 1-oxyl (5j) (TEMPO). The amount of the nitroxide radical compound used is stoichiometrically preferably 0.01 to 0.3 molar equivalents, more preferably 0.03 to 0.1 molar equivalents, with respect to compound (3a-1).

The reaction temperature differs depending on the reactive substrate and also differs depending on the stability or reactivity of the aromatic diazonium salt such that a high temperature (180° C.) is required for, for example, Balz-Schiemann reaction shown in the preceding literature (Balz, G. Schiemann, G., Chem. Ber. 1927, 60, 1186.). Since the aromatic diazonium salt has generally low stability and is highly reactive, the reaction proceeds at a relatively low temperature. The reaction temperature is preferably 70° C. or lower, more preferably 50° C. or lower, even more preferably 25° C. or lower. Alternatively, 0 to 10° C. is preferred for some substrates. The reaction time is usually within 10 hours. Preferably, the endpoint of the reaction is confirmed by HPLC or the like.

Preferably, this reaction is performed under a stream of inert gas such as nitrogen or argon.

Since excessive acid is used, an aqueous alkali solution is added to the reaction mixture to render the solution alkaline as a work-up procedure after completion of the reaction, followed by extraction of the compound of interest with an organic solvent. The extraction solvent is preferably toluene or the like.

The present invention further relates to, as shown in [Scheme 2] below,
a one-pot process for preparing a substituted aromatic compound or a salt thereof, comprising treating an aromatic amino compound or a salt thereof with a diazotization reagent in the presence of a source material for the substituent and a nitroxide radical compound or a salt thereof.

[Scheme 2]

[Formula 42]

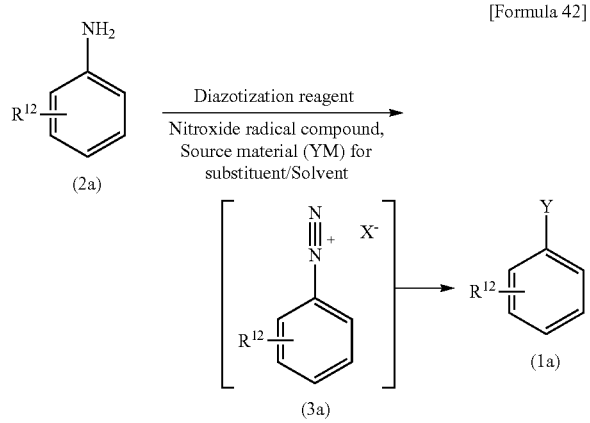

wherein the diazotization reagent and the nitroxide radical compound are as defined above; $X^-$ represents $HSO_4^-$, $NO_3^-$, $Cl^-$, $Br^-$, $I^-$, $ClO_4^-$, $BF_4^-$, or $PF_4^-$; the source material "YM" for the substituent represents hydrogen halide, alkali metal halide, hydrogen cyanide, sodium cyanide, potassium cyanide, sulfuric acid, potassium sulfite, sodium sulfite, sodium bisulfate, sodium nitrite, potassium nitrite, hypophosphorous acid, or a hydroxyaryl derivative; and $R^{12}$ represents a hydrogen atom or represents one or more identical or different organic groups as substituents on the benzene ring, wherein the substituents are not particularly limited by their types as long as the reaction is not inhibited.

The following [Scheme 2a] represents a process for preparing bromobenzene as a specific example of [Scheme 2]:

[Scheme 2a]

[Formula 43]

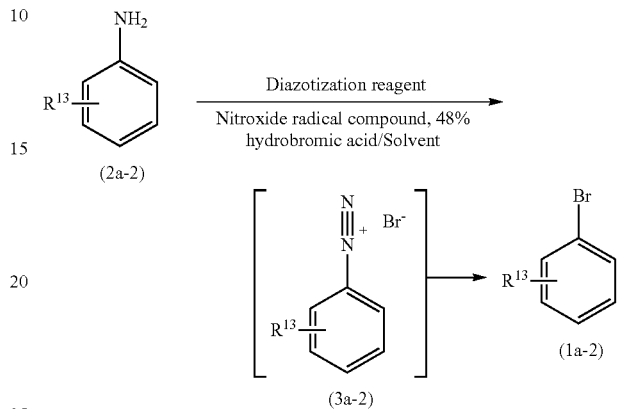

wherein the nitroxide radical compound and YM are as defined above; and $R^{13}$ represents a hydrogen atom or represents one or more identical or different organic groups as substituents on the benzene ring, wherein the substituents are not particularly limited by their types as long as the reaction is not inhibited.

Compound (2a-2) (aniline derivative) or a salt thereof can be treated with a diazotization reagent in the presence of 48% hydrobromic acid and the nitroxide radical compound in a solvent so that the substitution reaction proceeds simultaneously with the formation of aromatic diazonium salt (3a-2) to produce a bromobenzene (1a-2) derivative. Since most aromatic diazonium salts (3) are compounds that are highly reactive and thus have low stability, a preferred process for preparing compound (1a-2) of interest according to [Scheme 2a] causes the substitution reaction to proceed simultaneously with the in situ formation of aromatic diazonium salt (3) in the reaction system.

The solvent used in the reaction is not particularly limited as long as the reaction is not inhibited. Water, alcohol solvents, the polar solvent dimethyl sulfoxide, and nitrile solvents such as acetonitrile are preferably used alone or as a mixed solvent. Water, an aqueous alcohol solvent, and/or aqueous acetonitrile are particularly preferred. The amount of the solvent used is not particularly limited and is preferably 8 to 50 parts by volume (V/W), more preferably 10 to 20 parts by volume (V/W), with respect to 1 part of compound (2a-2).

The amount of the 48% hydrobromic acid used is stoichiometrically preferably 2 to 10 molar equivalents, more preferably 3 to 5 molar equivalents, with respect to compound (2a-2).

The diazotization reagent used can be any of those described above and is preferably alkali metal nitrite, more preferably sodium nitrite. The alkali metal nitrite is preferably used as an aqueous solution in the reaction.

The nitroxide radical compound used is preferably any of those described above and is preferably 4-hydroxy-2,2,6,6-tetramethylpiperidine 1-oxyl (5h) (TEMPOL) or 2,2,6,6-tetramethylpiperidine 1-oxyl (5j) (TEMPO). The amount of the nitroxide radical compound used is stoichiometrically preferably 0.01 to 0.5 molar equivalents, more preferably 0.01 to 0.3 molar equivalents, even more preferably 0.03 to 0.1 molar equivalents, with respect to compound (2a-2).

The reaction temperature can be in the range of room temperature to the boiling point of the solvent according to the reactive substrate and is preferably 55° C. or lower, more preferably room temperature to 55° C. The reaction time is usually within 10 hours. Preferably, the endpoint of the reaction is confirmed by HPLC or the like.

Preferably, this reaction is performed under a stream of inert gas such as nitrogen or argon.

Hereinafter, another preferable aspect of the present invention will be described.

A specific FXa inhibitor according to the present specification is preferably, for example, compound (E) described above. Compound (E) may be a free form (free base) or a hydrate thereof or may be a pharmacologically acceptable salt or a hydrate of the salt.

Examples of the salt of compound (E) include hydrochloride, sulfate, hydrobromide, hydroiodide, phosphate, nitrate, benzoate, methanesulfonate, 2-hydroxyethanesulfonate, p-toluenesulfonate, acetate, propanoate, oxalate, malonate, succinate, glutarate, adipate, tartrate, maleate, fumarate, malate, and mandelate.

The salt of compound (E) is preferably hydrochloride or p-toluenesulfonate, with
p-toluenesulfonate being particularly preferred.

Compound (E) or a salt thereof, or a hydrate thereof is preferably
$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide;
$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide hydrochloride;
$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide mono-p-toluenesulfonate; or
$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide mono-p-toluenesulfonate monohydrate, with
$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide mono-p-toluenesulfonate monohydrate (E-a) being particularly preferred.

[Formula 44]

(E-a)

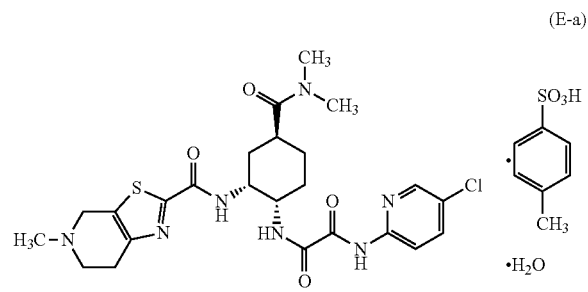

DETAILED DESCRIPTION

Hereinafter, the preparation process of the present invention will be described in detail.

A feature of the present invention is that nitroxide radical compound (5) is used as a catalyst in the preparation of bromo compound (11a) from amino compound (12) or a salt thereof.

The process for preparing compound (11a) from compound (12) will be described.

[Formula 45]

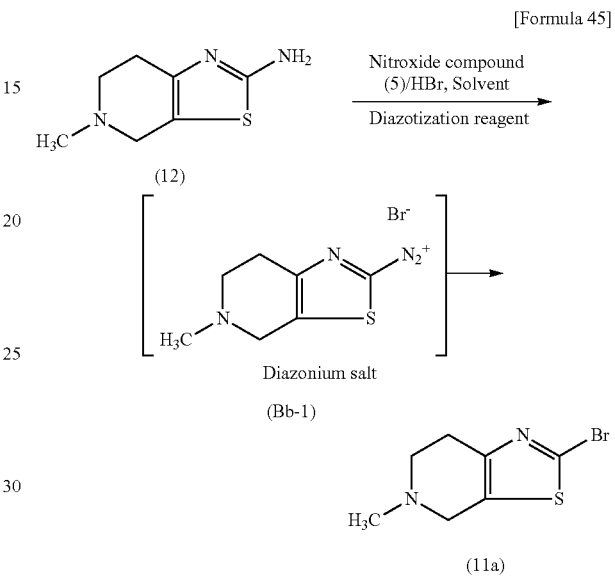

Compound (11a) is prepared by treatment with a solution of a diazotization reagent in the presence of hydrobromic acid and nitroxide compound (5) in a solvent.

Compound (12) used as a starting material may be used in the form of a free base or a salt, or a hydrate thereof. Its salt or a hydrate of the salt is preferred. The hydrate in the hydrate of the salt may not form crystallization water and may have adhesion water as long as the content of compound (12) is known. Since compound (12) is preferably added dropwise into the reaction system for use, the salt of compound (12) is preferably used as an aqueous solution containing the salt substantially dissolved in water.

The solvent used in the reaction is not particularly limited as long as the reaction is not inhibited. Water, an alcohol solvent, and/or the polar solvent dimethyl sulfoxide are preferred. Water is particularly preferred. The amount of the solvent used is not particularly limited and is preferably 8 to 50 parts by volume (V/W), more preferably 10 to 15 parts by volume (V/W), with respect to 1 part of compound (12).

The hydrogen bromide used in the reaction can be an aqueous hydrobromic acid solution and is, preferably, widely commercially available 48% hydrobromic acid. The amount of the 48% hydrobromic acid used is stoichiometrically preferably 2 to 20 molar equivalents, more preferably 3 to 10 molar equivalents, even more preferably 5 to 7 molar equivalents, with respect to compound (12).

Examples of the diazotization reagent used in the reaction can include nitrous acid, alkali metal nitrite, alkaline earth metal nitrite, and C1-C8 alkyl ester of nitrous acid. The alkali metal nitrite is preferably sodium nitrite or potassium nitrite. The alkaline earth metal nitrite is preferably calcium nitrite, barium nitrite, or the like. The C1-C8 alkyl ester of nitrous acid is preferably nitrous acid ethyl ester, nitrous acid n-propyl ester, nitrous acid isopropyl ester, nitrous acid n-butyl ester, nitrous acid isobutyl ester, nitrous acid t-butyl ester, nitrous acid isoamyl ester, or the like. The diazotization reagent used can be any of those described above and is preferably alkali metal nitrite, more preferably sodium nitrite. The alkali metal nitrite is preferably used as an aqueous solution in the reaction.

The nitroxide radical compound used in the reaction is preferably any of those described above and is preferably 4-hydroxy-2,2,6,6-tetramethylpiperidine 1-oxyl (5h) (TEMPOL) or 2,2,6,6-tetramethylpiperidine 1-oxyl (5j) (TEMPO). The amount of the nitroxide radical compound used is stoichiometrically preferably 0.01 to 0.3 molar equivalents, more preferably 0.03 to 0.1 molar equivalents, with respect to compound (12).

The reaction temperature is preferably 25° C. or lower, more preferably 0 to 10° C. The dropwise addition time is preferably 2 to 10 hours. After completion of the dropwise addition, the reaction time is usually within 10 hours. Preferably, the endpoint of the reaction is confirmed by HPLC or the like.

Preferably, this reaction is performed under a stream of inert gas such as nitrogen or argon.

A more preferred embodiment of the preparation process shown in the scheme preferably involves adding dropwise an aqueous solution of compound (12) and a diazotization reagent into a solution of 48% hydrobromic acid and a nitroxide radical compound in water as a solvent. The dropwise addition is preferably performed under a stream of inert gas such as nitrogen or argon. Amount, time, and temperature in this preferred embodiment are as described above.

The reaction solvent is not particularly limited as long as the reaction is not inhibited. Water, an alcohol solvent, and/or the polar solvent dimethyl sulfoxide are preferred. Water is particularly preferred. The amount of the solvent used is not particularly limited and is preferably 8 to 50 parts by volume (V/W), more preferably 10 to 20 parts by volume (V/W), with respect to 1 part of compound (12).

The amount of the 48% hydrobromic acid used is stoichiometrically preferably 2 to 10 molar equivalents, more preferably 3 to 5 molar equivalents, with respect to compound (12).

Examples of nitroxide radical compound (5) according to the present specification can include those described above. Nitroxide radical compound (5) is preferably one or two or more compounds selected from the group consisting of 3-carboxy-2,2,5,5-tetramethyl-1-pyrrolidine 1-oxyl (5d);
3-carbamoyl-2,2,5,5-tetramethylpyrrolidine 1-oxyl (5e);
3-carbamoyl-2,2,5,5-tetramethyl-3-pyrroline 1-oxyl (5f);
4-oxo-2,2,6,6-tetramethylpiperidinoxyl (5g);
4-hydroxy-2,2,6,6-tetramethylpiperidine 1-oxyl (5h);
4-acetamido-2,2,6,6-tetramethylpiperidine 1-oxyl (5i);
2,2,6,6-tetramethylpiperidine 1-oxyl (5j);
3-(maleimidomethyl)-proxyl (5k);
N-(1-oxyl-2,2,6,6-tetramethyl-4-piperidinyl)maleimide(5l); and
1-methyl-2-azaadamantane N-oxyl (5m),
with
4-hydroxy-2,2,6,6-tetramethylpiperidine 1-oxyl (5h: TEMPOL); or 2,2,6,6-tetramethylpiperidine 1-oxyl (5j: TEMPO) being particularly preferred.

The amount of the nitroxide radical compound used is stoichiometrically of the order of preferably 0.01 to 0.3 molar equivalents, more preferably 0.03 to 0.1 molar equivalents, with respect to compound (12).

The reaction temperature is preferably 25° C. or lower, more preferably 0 to 10° C. The dropwise addition time is preferably 2 to 10 hours. After completion of the dropwise addition, the reaction time is usually within 10 hours. Preferably, the endpoint of the reaction is confirmed by HPLC or the like.

Preferably, this reaction is performed under a stream of inert gas such as nitrogen or argon.

Since excessive acid is used, an aqueous alkali solution is added to the reaction mixture as a work-up procedure after completion of the reaction, followed by extraction with an organic solvent. The extraction solvent is preferably toluene.

A further preferred aspect of the preparation of compound (11) of the present invention will be described.

[Formula 46]

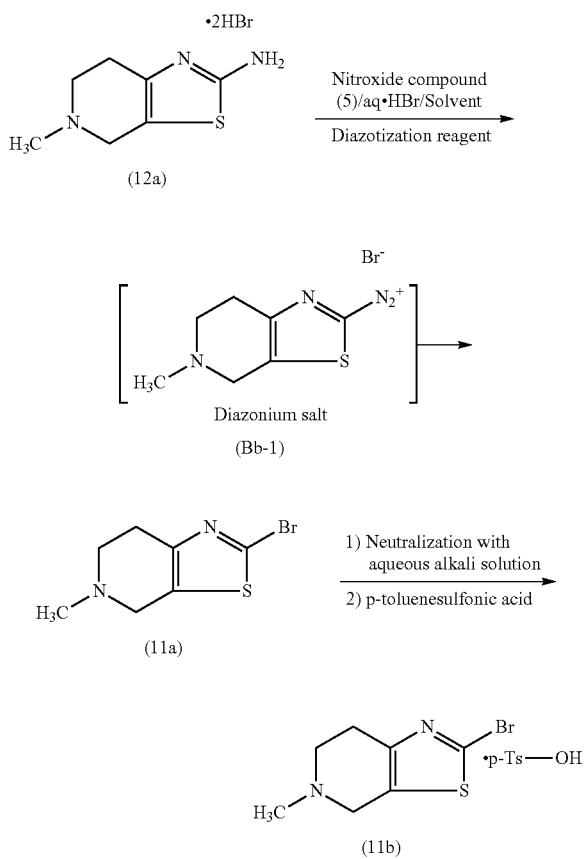

Since diazonium salt (B) formed in situ as an intermediate in the reaction is highly reactive and generally very unstable, diazonium salt (B) is preferably converted to compound (11a) simultaneously with its formation. Thus, preferably, compound (12) is treated with a diazotization reagent in the presence of nitroxide radical compound (5). In this context, the present invention encompasses even a process for preparing compound (11a) by isolating diazonium salt (B).

Hereinafter, preferred procedures will be described.

[Step 1]:

Hydrobromic acid is dissolved in water as a solvent. Into this aqueous solution, a nitroxide radical compound or a salt thereof is added and dissolved to prepare a solution, which is then cooled to 10° C. or lower, preferably to approximately 0 to 5° C., and stirred.

[Step 2]:
(a) Dihydrobromide compound (12a) represented by the following formula (12a)
or a hydrate of the salt:

[Formula 47]

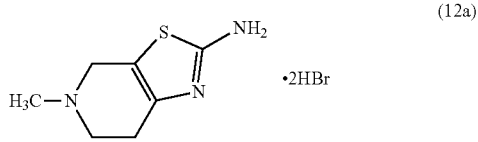

(12a)

is substantially dissolved in water used as a solvent to prepare an aqueous solution, and
(b) alkali metal nitrite or alkaline earth metal nitrite, preferably alkali metal nitrite, is dissolved in water as a solvent to prepare an aqueous solution.

These (a) and (b) are simultaneously added into the solution of [Step 1] at 10° C. or lower, preferably in the range of approximately 0 to 10° C., under a nitrogen or argon gas atmosphere, preferably under a nitrogen gas atmosphere. After completion of the addition, the mixture is stirred at this temperature to prepare compound (11a) or a salt thereof. This process is more preferred.

The reagent used is as described above. The simultaneous addition can be the simultaneous initiation of the addition. The addition time is of the order of preferably 2 to 10 hours, more preferably 2 to 5 hours. In the simultaneous addition, the completion time lag between the addition of (a) and the addition of (b) is preferably approximately 1 hour, more preferably approximately 30 minutes.

Since compound (12) is preferably added dropwise into the reaction system for use as shown in the scheme above, the salt of compound (12) is preferably used as an aqueous solution containing the salt substantially dissolved in water and is preferably dihydrobromide compound (12a). Since compound (12a) is used as an aqueous solution, its hydrate may be used or its adhesion water may be hydrated.

Compound (11a) prepared by this preparation process assumes an HBr salt in the presence of an excess of hydrobromic acid. The HBr salt of compound (11a) may be used without problems. For removing a small excess of the diazotization reagent or the like to isolate compound (11a) as stable crystals, it is more preferred to subsequently neutralize the resulting compound with an aqueous alkali solution, followed by treatment with p-toluenesulfonic acid to convert compound (11a) to its mono-p-toluenesulfonate compound (11b), which is then isolated.

After the reaction described above, an aqueous alkali solution is added to the reaction mixture at 20° C. or lower to render the mixed solution alkaline. The free salt compound (11a) formed is extracted with an organic solvent.

The aqueous alkali solution used can be an aqueous solution of alkali metal hydroxide, carbonate, or the like and is preferably an aqueous solution of sodium hydroxide. Its concentration is preferably a high concentration for reducing the amount of the aqueous alkali solution added. Approximately 25% aqueous sodium hydroxide solution is preferred. For rendering the solution alkaline, the pH can be 13 or higher.

The organic solvent used in the extraction is preferably toluene. The extraction is performed several times. The resulting extracts are combined and concentrated to distil off the solvent.

Next, compound (11a) is treated with p-toluenesulfonic acid to prepare its mono-p-toluenesulfonate compound (11b).

To the concentrated residue of the extracts, an organic solvent is added, and a solution of commercially available p-toluenesulfonic acid monohydrate is then added.

The organic solvent added to the residue is preferably a hydrocarbon solvent, a C1-C4 alcohol solvent, a C2-C4 nitrile solvent, or the like. A mixed solvent of these solvents may be used. Among these solvents, a combination of toluene with an alcohol solvent such as methanol, ethanol, or 2-propanol is preferred. A combination of toluene with methanol is more preferred.

The organic solvent for preparing the solution of p-toluenesulfonic acid monohydrate is preferably any of the alcohol solvents described above, more preferably methanol.

Hereinafter, a specific preferred aspect of the preparation of compound (11b) will be described.

Methanol and toluene are added to the residue containing compound (11a) as a crude product. The amounts of methanol and toluene added are preferably of the order of 2 to 5 parts by volume (V/W) and 8 to 30 parts by volume (V/W), respectively, with respect to 1 part by weight of compound (11a).

A solution of p-toluenesulfonic acid monohydrate in methanol is added dropwise into the mixed solution of the residue in methanol and toluene. The amount of methanol for preparing the methanol solution is preferably 3 to 5 parts by volume (V/W) with respect to 1 part by weight of compound (11a). The addition can be performed at a temperature of 35° C. or lower.

After the addition, the mixed solution is stirred at 0 to 5° C. to completely crystallize compound (11b). The precipitated crystals can be filtered, washed, and dried to prepare compound (11b) represented by the following formula (11b):

[Formula 48]

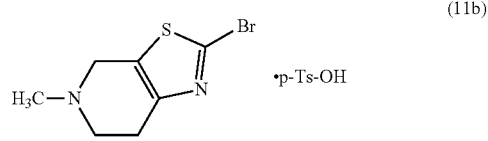

(11b)

The present application further relates to the preparation of compound (13a) which is important as an intermediate for preparation of FXa inhibitor compound (E-a). Compound (13a) can be prepared from compound (11b) prepared in the present invention according to a preparation process (scheme shown below) described in the specification of International Publication No. WO 2005/047296. This process will be described later in the Reference Examples.

[Formula 49]

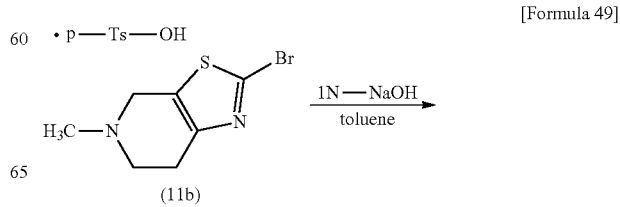

(11b)

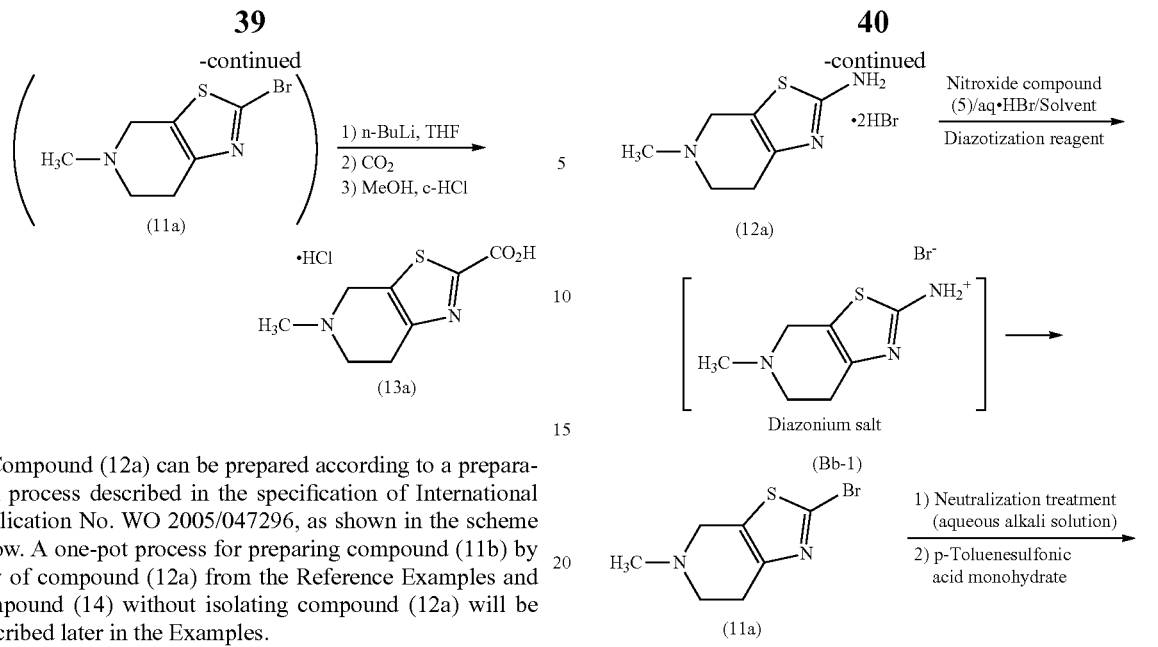

Compound (12a) can be prepared according to a preparation process described in the specification of International Publication No. WO 2005/047296, as shown in the scheme below. A one-pot process for preparing compound (11b) by way of compound (12a) from the Reference Examples and compound (14) without isolating compound (12a) will be described later in the Examples.

[Formula 50]

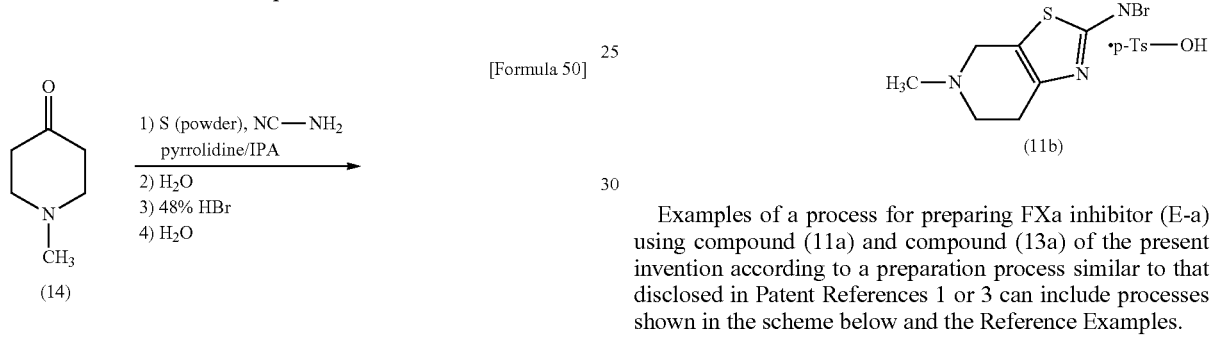

Examples of a process for preparing FXa inhibitor (E-a) using compound (11a) and compound (13a) of the present invention according to a preparation process similar to that disclosed in Patent References 1 or 3 can include processes shown in the scheme below and the Reference Examples.

[Formula 51]

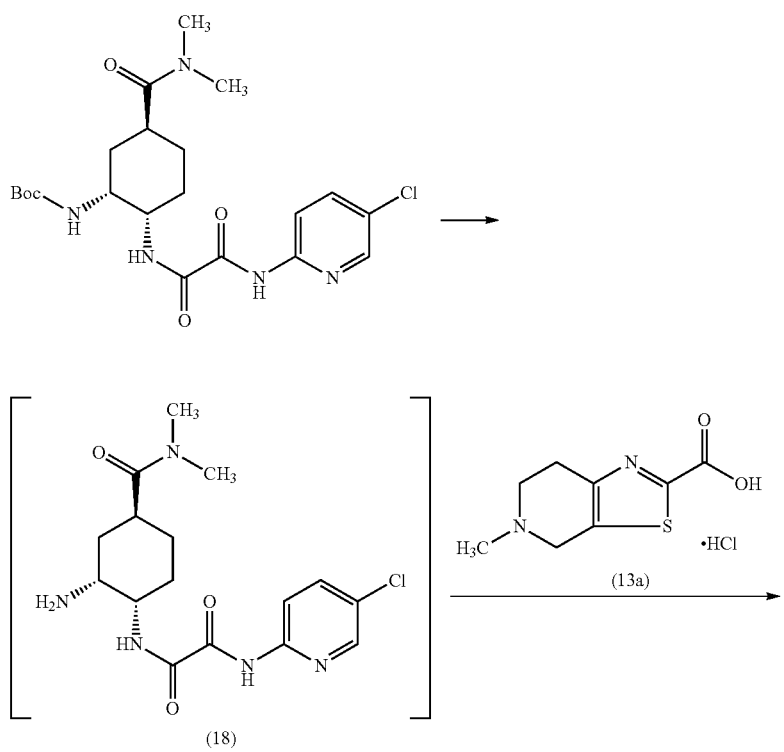

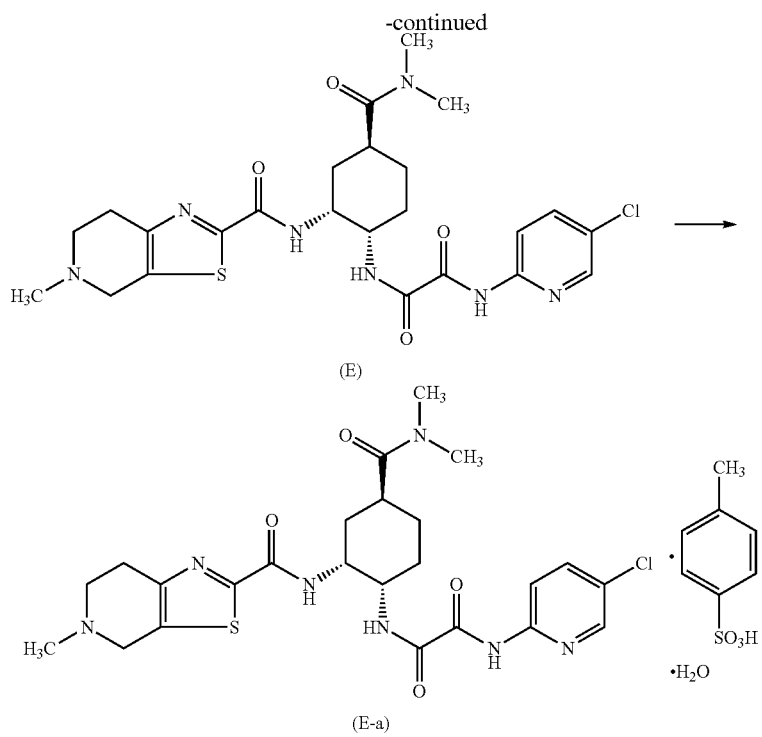

wherein Boc is as defined above.

EXAMPLES

Next, the present invention will be described in detail with reference to the Examples. However, the present invention is not intended to be limited to these in any way.

Tetramethylsilane was used as the internal standard for the nuclear magnetic resonance (NMR) spectra. Abbreviations showing multiplicity represent s=singlet, d=doublet, t=triplet, q=quartet, m=multiplet, and brs=broad singlet.

Example 1

3-Bromonitrobenzene (1c)

[Formula 52]

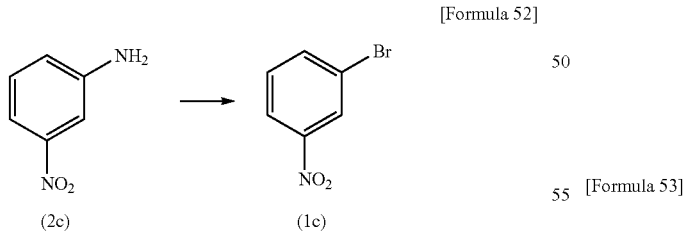

Water (45 ml), acetonitrile (6 ml), and 48% hydrobromic acid (27 ml) were added to 3-nitroaniline (2c) (2.76 g, 20 mmol) at room temperature. To the mixed solution, 2,2,6,6-tetramethylpiperidine 1-oxyl (0.31 g, 2 mmol) was added at room temperature, and the mixture was cooled to 10° C. or lower. Then, sodium nitrite (2.07 g) dissolved in water (15 ml) was added thereto. After stirring at room temperature for approximately 2 hours, a 10 mol/L aqueous sodium hydroxide solution (30 ml) was added thereto, and the precipitated crystals were collected by filtration, washed with water (40 ml), and then dried under reduced pressure to obtain 3-bromonitrobenzene (1c) (3.75 g, 93.0%). The instrumental spectrum data and HPLC retention time (Rt) of the obtained compound (1c) were completely consistent with those of the commercially available compound (1c).

Likewise, these procedures were performed under the same reaction conditions as above except that CuBr (2 mmol) was added or not added instead of 2,2,6,6-tetramethylpiperidine 1-oxyl. As a result, the yield of product (1c) was 36% for the addition of CuBr (2 mmol) and 12% for the non-addition thereof. Meanwhile, these procedures were also performed under similar conditions except that: CuBr (2 mmol) was added or not added instead of 2,2,6,6-tetramethylpiperidine 1-oxyl; the reaction temperature was not room temperature but was raised to 70 to 80° C.; and the reaction time was 18 hours for stirring. As a result, the yield was 90% in both cases. This demonstrated that reaction with a nitroxide radical compound as a catalyst proceeded at a low temperature in a short time.

Example 2

4-Bromobenzonitrile (1d)

[Formula 53]

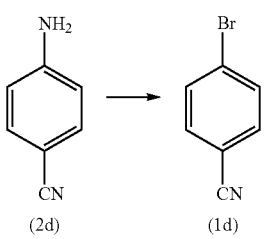

Water (45 ml) and 48% hydrobromic acid (27 ml) were added to 4-aminobenzonitrile (2d) (2.36 g, 20 mmol) at room temperature. To the mixed solution, 2,2,6,6-tetramethylpiperidine 1-oxyl (0.31 g, 2 mmol) was added at room temperature, and the mixture was cooled to 10° C. or lower. Then, sodium nitrite (2.07 g) dissolved in water (15 ml) was added thereto. The mixture was heated to 55° C., then stirred for approximately 2 hours, and cooled to room temperature. Then, a 10 mol/L aqueous sodium hydroxide solution (40 ml) was added thereto, followed by extraction twice with toluene (300 ml). The toluene layers were combined and washed with water (50 ml). The solvent was distilled off by the concentration of the toluene layer under reduced pressure to obtain 4-bromobenzonitrile (1d) (3.35 g, 83.0%). The instrumental spectrum data and HPLC retention time (Rt) of the obtained compound (1d) were completely consistent with those of the commercially available compound (1d).

Likewise, these procedures were performed under the same reaction conditions as above except that CuBr (2 mmol) was added or not added instead of 2,2,6,6-tetramethylpiperidine 1-oxyl. As a result, the yield of product (1d) was 80% for the addition of CuBr (2 mmol) and 60% for the non-addition thereof. By contrast, the raised reaction temperature under conditions involving the non-addition thereof did not show improvement in yield.

Example 3

3-Bromo-2-chloropyridine (7)

[Formula 54]

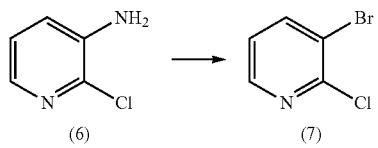

Water (45 ml) and 48% hydrobromic acid (27 ml) were added to 3-amino-2-chloropyridine (6) (2.57 g, 20 mmol) at room temperature. To the mixed solution, 2,2,6,6-tetramethylpiperidine 1-oxyl (0.31 g, 2 mmol) was added at room temperature, and the mixture was cooled to 10° C. or lower. Then, sodium nitrite (4.14 g) dissolved in water (30 ml) was added thereto. After stirring at room temperature for approximately 2 hours, a 10 mol/L aqueous sodium hydroxide solution (40 ml) was added thereto, followed by extraction twice with toluene (300 ml). The toluene layers were combined and washed with water (50 ml). The solvent was distilled off by the concentration of the toluene layer under reduced pressure to obtain 3-bromo-2-chloropyridine (7) (3.08 g, 80.1%). The instrumental spectrum data and HPLC retention time (Rt) of the obtained compound (7) were completely consistent with those of the commercially available compound (7).

Likewise, these procedures were performed except that CuBr (2 mmol) was added or not added instead of 2,2,6,6-tetramethylpiperidine 1-oxyl. As a result, the yield of product (7) was 40% and 30%, respectively. This demonstrated that use of a nitroxide radical compound as a catalyst drastically improved yields.

Reference Example 1

2-Amino-5-methyl-4,5,6,7-tetrahydrothiazolo[5,4-c]pyridine (12)

[Formula 55]

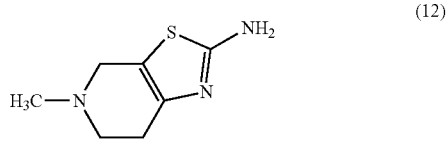

A solution of cyanamide (67.0 g) in 2-propanol (360 mL) and sulfur powders (51.0 g) were added in this order to a solution of 1-methyl-4-piperidone (14) (180.0 g) in 2-propanol (1.44 L) heated to 50° C. A catalytic amount of pyrrolidine (13.3 mL) was added thereto, and the mixture was stirred at 50° C. or higher for 2 hours, then allowed to cool to room temperature, and stirred overnight. The reaction mixture was cooled to 10° C. or lower in an ice water bath and stirred at this temperature for 1 hour. The precipitated crystals were filtered, washed with 2-propanol (540 mL), and dried under reduced pressure at 40° C. to obtain the title compound (12) (209.9 g).

$^1$H-NMR (CDCl$_3$) δ ppm: 4.86 (br, 2 H), 3.47-3.46 (t, 2 H, J=1.9 Hz), 2.78-2.71 (m, 2 H), 2.71-2.65 (m, 2 H), 2.47 (s, 3 H).

MS (FAB) m/z: 170 (M+H)$^+$.
Anal.: C$_7$H$_{11}$N$_3$S
Theoretical: C, 49.68; H, 6.55; N, 24.83; S, 18.95.
Found: C, 49.70; H, 6.39; N, 24.91; S, 19.00.

Reference Example 2

2-Amino-5-methyl-4,5,6,7-tetrahydrothiazolo[5,4-c]pyridine dihydrobromide (12a)

[Formula 56]

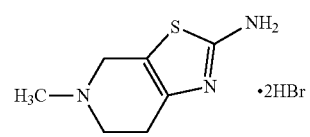

1-Methyl-4-piperidone (14) (100.0 g) was dissolved in 2-propanol (800 mL) at room temperature. Then, the solution was heated in a hot water bath to raise the internal temperature to 50° C. A solution of cyanamide (37.16 g) in 2-propanol (200 mL) and sulfur powders (28.34 g) were added in this order thereto at 50° C. A catalytic amount of pyrrolidine (7.4 mL) was added thereto, and the mixture was stirred at 50 to 64° C. for 1 hour and then allowed to cool to room temperature. After dropwise addition of 48% hydrobromic acid (358.0 g) at 30 to 40° C., the mixture was cooled to 10° C. or lower in an ice water bath and stirred at this temperature for 1.5 hours. The precipitated crystals were filtered, washed with 2-propanol (500 mL), and dried under reduced pressure at 40° C. to obtain the title compound (12a) (258.2 g).

$^1$H-NMR (D$_2$O) δ ppm: 4.45-4.53 (d, 1 H, J=15.2 Hz), 4.20-4.26 (d, 1 H, J=15.2 Hz), 3.75-3.90 (m, 1 H), 3.50-3.67 (m, 1 H), 3.10 (s, 3 H), 2.91-3.18 (m, 2 H).

Anal.: C$_7$H$_{13}$Br$_2$N$_3$S
Theoretical: C, 25.39; H, 3.96; Br, 48.27; N, 12.69; S, 9.69.
Found: C, 25.54; H, 3.93; Br, 48.09; N, 12.62; S, 9.72.

Reference Example 3

2-Bromo-5-tert-butoxycarbonyl-4,5,6,7-tetrahydrothiazolo[5,4-c]pyridine (Japanese Patent Laid-Open No. 2001/294572)

[Formula 57]

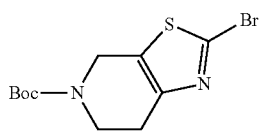

Cupric bromide (1.05 g, 4.7 mmol) was suspended in N,N-dimethylformamide, and tert-butyl nitrite (696 mg, 6.5 mmol) was added to the suspension. 2-Amino-5-tert-butoxycarbonyl-4,5,6,7-tetrahydrothiazolo[5,4-c]pyridine (1.00 g, 5.9 mmol) was added thereto under ice cooling, and the reaction solution was then stirred under heating at 40° C. for 30 minutes. The reaction solution was concentrated under reduced pressure, and the residue was purified by silica gel column chromatography (ethyl acetate:hexane=1:5) to obtain the title compound (568 mg, 41%) as a yellow solid.

$^1$H NMR (CDCl$_3$) 1.48 (9 H, s), 2.85 (2 H, br s), 3.72 (2 H, t, J=5.6 Hz), 4.56 (2 H, br s).

MS (FAB) m/z 319 (M+H)$^+$.

Reference Example 4

Synthesis of 2-bromo-5-methyl-4,5,6,7-tetrahydrothiazolo[5,4-c]pyridine (11a) (International Publication No. WO 2005/047296)

[Formula 58]

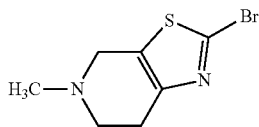

2-Amino-5-methyl-4,5,6,7-tetrahydrothiazolo[5,4-c]pyridine (12) (600.0 g, 3.545 mol) was suspended in water (6.0 L), and 48% hydrobromic acid (4.2 L) was then added dropwise to the suspension at 5 to 15° C. A solution of sodium nitrite (367.2 g, 3.56 mol) in water (1.8 L) was added dropwise at 0 to 5° C. over 1.5 hours, and the mixture was then heated to 30° C. and stirred for 24 hours. The reaction mixture was rendered strongly alkaline (pH=12.5) by neutralization with a 5 N aqueous sodium hydroxide solution (6.0 L), and the aqueous layer was then subjected to extraction twice with toluene (12.0 L and 6.0 L). The toluene layers were combined and dried over anhydrous sodium sulfate (1202.0 g). Then, insoluble matter was filtered off, and the mother liquor was concentrated under reduced pressure at 40° C. to obtain the title compound (11a) (557.6 g, 67.5%).

$^1$H-NMR (CDCl$_3$) δ ppm: 3.58-3.57 (t, 3 H, J=1.8 Hz), 2.92-2.87 (m, 2 H), 2.81-2.76 (m, 2 H), 2.49 (s, 3 H).

Reference Example 5

Synthesis of 2-bromo-5-methyl-4,5,6,7-tetrahydrothiazolo[5,4-c]pyridine p-toluenesulfonate (11b) (International Publication No. WO 2005/047296)

[Formula 59]

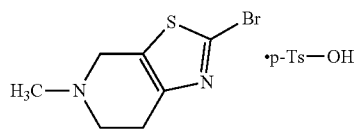

2-Amino-5-methyl-4,5,6,7-tetrahydrothiazolo[5,4-c]pyridine dihydrobromide (12a) (50.01 g, 0.151 mol) was added and suspended in a mixed solution of water (250 mL) and 48% hydrobromic acid (175 mL) at room temperature. This suspension was cooled to an internal temperature of 10° C. or lower, and a solution of sodium nitrite (15.63 g, 0.152 mol) in water (75 mL) was then added dropwise thereto over 1.5 hours with the internal temperature kept at 10° C. or lower. The mixture was stirred at 10° C. or lower for 20 hours and then rendered alkaline by the dropwise addition of a 10 N aqueous sodium hydroxide solution (175 mL) with the temperature kept at 20° C. or lower. The resulting solution had a pH of 13.1. Subsequently, the aqueous layer was subjected to extraction twice with toluene (375 mL and 250 mL), and ¼ of the combined toluene layer was used in the subsequent procedures. The toluene layer was concentrated, and the concentrated residue was then dissolved in methanol (43.8 mL). A solution of p-toluenesulfonic acid monohydrate (5.03 g) in methanol (18.8 mL) was added dropwise thereto at room temperature, and the mixture was then cooled to 10° C. or lower and stirred at this temperature for 1.5 hours. The precipitated crystals were filtered, washed with methanol (18.8 mL), and dried under reduced pressure at 40° C. to obtain the title compound (11b) (9.05 g, 14.8%).

$^1$H-NMR (DMSO-d$_6$) δ ppm: 10.15 (br, 1 H), 7.47-7.43 (d, 2 H, J=8.2 Hz), 7.09-7.07 (d, 2 H, J=8.2 Hz), 4.47 (s, 2 H), 3.58 (s, 2 H), 3.04 (t, 2 H, J=6.1 Hz), 2.96 (s, 3 H), 2.29 (s, 3 H).

Anal.: C$_{14}$H$_{17}$BrN$_2$O$_3$S$_2$

Theoretical: C, 41.48; H, 4.23; Br, 19.71; N, 6.91; S, 15.82. Found: C, 41.54; H, 4.18; Br, 19.83; N, 7.03; S, 16.02.

Reference Example 6

Tert-butyl [(1R,2S,5S)-2-({[(5-chloropyridin-2-yl)amino](oxo)acetyl}amino)-5-(dimethylaminocarbonyl)cyclohexyl]carbamate (17)

[Formula 60]

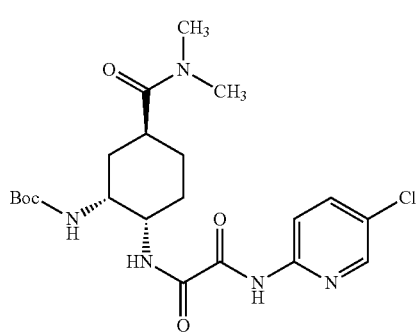

wherein Boc represents a tert-butoxycarbonyl group.

Triethylamine (169 ml) was added to a suspension of tert-butyl (1R,2S,5S)-2-amino-5-(dimethylaminocarbonyl)cyclohexylcarbamate monooxalate (100.1 g) in acetonitrile (550 ml) at 60° C. 2-[(5-Chloropyridin-2-yl)amino]-2-oxoacetate monohydrochloride (84.2 g) was added thereto at this temperature, and the mixture was stirred for 6 hours and then stirred at room temperature for 16 hours. To the reaction solution, water was added, and the mixture was stirred at 10° C. for 1.5 hours. Then, the crystals were collected by filtration to obtain the title compound (17) (106.6 g).

$^1$H-NMR (CDCl$_3$) δ: 1.25-1.55 (2 H, m), 1.45 (9 H, s), 1.60-2.15 (5 H, m), 2.56-2.74 (1 H, br. s), 2.95 (3 H, s), 3.06 (3 H, s), 3.90-4.01 (1 H, m), 4.18-4.27 (1 H, m), 4.70-4.85 (0.7 H, br), 5.70-6.00 (0.3 H, br. s), 7.70 (1 H, dd, J=8.8, 2.4 Hz), 7.75-8.00 (1 H, br), 8.16 (1 H, br. d, J=8.8 Hz), 8.30 (1 H, d, J=2.4 Hz), 9.73 (1 H, s).

Reference Example 7

N$^1$-(5-chloropyridin-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide (E)

[Formula 61]

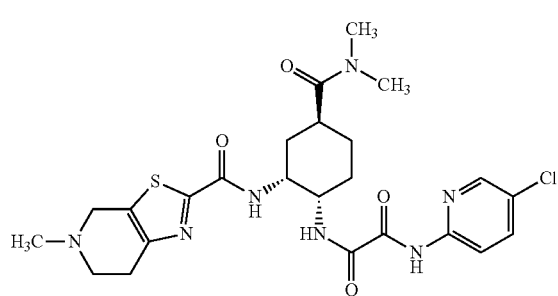

(E)

Methanesulfonic acid (66 ml) was added to a suspension of tert-butyl [(1R,2S,5S)-2-({[(5-chloropyridin-2-yl)amino](oxo)acetyl}amino)-5-(dimethylaminocarbonyl)cyclohexyl]carbamate (17) (95.1 g) in acetonitrile (1900 ml) at room temperature, and the mixture was stirred at this temperature for 2 hours. To the reaction solution, triethylamine (155 ml), 5-methyl-4,5,6,7-tetrahydro[1,3]thiazolo[5,4-c]pyridine-2-carboxylic acid hydrochloride (13a) (52.5 g), 1-hydroxybenzotriazole (33.0 g), and 1-ethyl-3-(3-dimethylaminopropyl)carbodiimide hydrochloride (46.8 g) were added under ice cooling, and the mixture was stirred at room temperature for 16 hours. Triethylamine and water were added thereto, and the mixture was stirred for 1 hour under ice cooling. Then, the crystals were collected by filtration to obtain the title compound (E) (103.2 g).

$^1$H-NMR (CDCl$_3$) δ: 1.60-1.98 (3 H, m), 2.00-2.16 (3 H, m), 2.52 (3 H, s), 2.78-2.90 (3 H, m), 2.92-2.98 (2 H, m), 2.95 (3 H, s), 3.06 (3 H, s), 3.69 (1 H, d, J=15.4 Hz), 3.75 (1 H, d, J=15.4 Hz), 4.07-4.15 (1 H, m), 4.66-4.72 (1 H, m), 7.40 (1 H, dd, J=8.8, 0.6 Hz), 7.68 (1 H, dd, J=8.8, 2.4 Hz), 8.03 (1 H, d, J=7.8 Hz), 8.16 (1 H, dd, J=8.8, 0.6 Hz), 8.30 (1 H, dd, J=2.4, 0.6 Hz), 9.72 (1 H, s).

MS (ESI) m/z: 548 (M+H)$^+$.

Reference Example 8

N$^1$-(5-chloropyridin-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide mono-p-toluenesulfonate monohydrate (E-a)

[Formula 62]

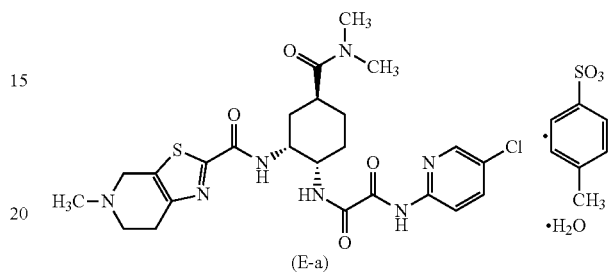

(E-a)

N$^1$-(5-Chloropyridin-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide (E) (6.2 g) was dissolved in methylene chloride (120 ml). To the solution, a 1 mol/L solution of p-toluenesulfonic acid in ethanol (11.28 ml) was added, and the solvent was distilled off. To the residue, 15% aqueous ethanol (95 ml) was added, and the mixture was dissolved by stirring at 60° C. Then, the mixture was cooled to room temperature and stirred for 1 day. The precipitated crystals were collected by filtration, washed with ethanol, and then dried under reduced pressure at room temperature for 2 hours to obtain the title compound (E-a) (7.4 g).

$^1$H-NMR (DMSO-d$_6$) δ: 1.45-1.54 (1 H, m), 1.66-1.78 (3 H, m), 2.03-2.10 (2 H, m), 2.28 (3 H, s), 2.79 (3 H, s), 2.91-3.02 (1 H, m), 2.93 (3 H, s), 2.99 (3 H, s), 3.13-3.24 (2 H, m), 3.46-3.82 (2 H, m), 3.98-4.04 (1 H, m), 4.43-4.80 (3 H, m), 7.11 (2 H, d, J=7.8 Hz), 7.46 (2 H, d, J=8.2 Hz), 8.01 (2 H, d, J=1.8 Hz), 8.46 (1 H, t, J=1.8 Hz), 8.75 (1H, d, J=6.9 Hz), 9.10-9.28 (1H, br), 10.18 (1H, br), 10.29 (1H, s).

MS (ESI) m/z: 548 (M+H)$^+$.

Anal.: C$_{24}$H$_{30}$ClN$_7$O$_4$S·C$_7$H$_8$O$_3$S·H$_2$O
Theoretical: C, 50.43; H, 5.46; N, 13.28, Cl; 4.80, S; 8.69.
Found: C, 50.25; H, 5.36; N, 13.32, Cl; 4.93, S; 8.79.

mp (dec.): 245-248° C.

Reference Example 9

5-Methyl-4,5,6,7-tetrahydrothiazolo[5,4-c]pyridine-2-carboxylic acid monohydrochloride (13a)

[Formula 63]

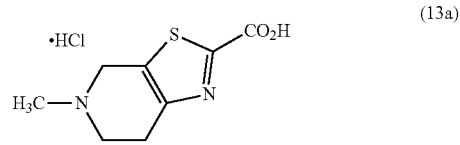

2-Bromo-5-methyl-4,5,6,7-tetrahydrothiazolo[5,4-c]pyridine p-toluenesulfonate (11b) (40.00 g) and a 1 N aqueous sodium hydroxide solution (200 mL) were mixed at room temperature and stirred for 30 minutes, and the aqueous layer was then subjected to extraction twice with toluene (400 mL×2). The combined organic layer was washed with 5% saline (200 mL). The organic layer was concentrated into 80 mL under reduced pressure at an external temperature of 50° C. or lower and then subjected to sampling for water content measurement (solution weight after concentration: 91.03 g, solution weight after sampling: 87.68 g). The water content of the sampled concentrate was measured using a Karl Fischer titrator and was consequently 0.0231% (weight ratio). The concentrate thus sampled was dissolved in anhydrous tetrahydrofuran (231 mL), and the atmosphere in the system was then changed to an argon atmosphere. The internal temperature was decreased to −30° C. or lower. Then, a 1.59 mol/L solution of n-butyllithium in n-hexane (61.7 mL) was added dropwise thereto with the internal temperature kept at −30° C. or lower, and the mixture was further stirred at this temperature for 1 hour. Carbon dioxide was absorbed to the system with the internal temperature kept at −30° C. or lower, and the reaction mixture was further stirred for 1 hour under the carbon dioxide atmosphere. The internal temperature was raised to 15° C., and the precipitated solid was then dissolved by the addition of methanol (193 mL). Concentrated hydrochloric acid (19.3 mL) was added dropwise thereto with the internal temperature kept at 20° C. or lower. The internal temperature was decreased to 10° C. or lower, and the reaction mixture was then stirred at this temperature for 1 hour. The precipitated crystals were filtered and washed with methanol (58 mL). The wet form was dried under reduced pressure at room temperature to obtain the title compound (13a) (21.20 g).

$^1$H-NMR (D$_2$O) δ ppm: 4.82-4.88 (d, 1H, J=16.0 Hz), 4.51-4.57 (d, 1H, J=16.0 Hz), 3.88-3.96 (m, 1H), 3.60-3.70 (m, 1H), 3.22-3.33 (m, 2H), 3.15 (s, 3H).

MS (EI) m/z: 198 (M)$^+$.

Anal.: C$_8$H$_{11}$ClN$_2$O$_2$S

Theoretical: C, 40.94; H, 4.72; Cl, 15.11; N, 11.94; S, 13.66.

Found: C, 40.83; H, 4.56; Cl, 14.81; N, 11.91; S, 13.87.

Example 4

2-Bromo-5-methyl-4,5,6,7-tetrahydrothiazolo[5,4-c]pyridine mono-p-toluenesulfonate (11b)

[Formula 64]

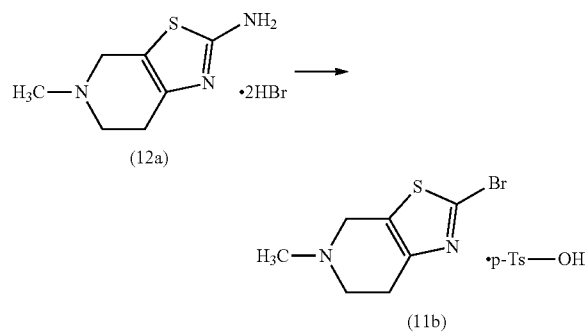

4-Hydroxy-2,2,6,6-tetramethylpiperidine 1-oxyl (TEMPOL) (22.83 g) was added and dissolved in a mixed solution of water (2700 mL) and 48% hydrobromic acid (1080 mL), and the resulting mixed solution was cooled to 0 to 5° C. To this mixed solution, a solution of 2-amino-5-methyl-4,5,6,7-tetrahydrothiazolo[5,4-c]pyridine dihydrobromide (12a) [746.06 g] dissolved in a mixed solution of 48% hydrobromic acid (209 mL) and water (2700 mL) and a solution of sodium nitrite (274.43 g) in water (1500 mL) were simultaneously added dropwise over 2 to 5 hours such that the internal temperature of the reaction solution was kept at 0 to 10° C. under a nitrogen stream in the reaction system. After completion of the dropwise addition, the reaction mixture was further stirred at 0 to 10° C. for 1 hour. The reaction mixture was rendered alkaline (pH>13) by the dropwise addition of a 25% aqueous sodium hydroxide solution (2400 mL) with the internal temperature kept at 20° C. or lower. Subsequently, the reaction mixture was subjected to extraction twice with toluene (3000 mL), and the toluene extract layer was concentrated. To the residue, methanol (600 mL) and toluene (2550 mL) were added, and the mixture was dissolved by stirring at 15 to 35° C. A solution of p-toluenesulfonic acid monohydrate (453.87 g) in methanol (900 mL) was added dropwise thereto at 15 to 35° C. over 30 minutes or longer, and the mixed solution was then cooled to 0 to 5° C. and stirred at 0 to 5° C. for 30 minutes or longer. The precipitated solid was filtered and washed with methanol (1350 mL) cooled to 0 to 5° C. The obtained solid was dried at 40° C. to obtain the title compound (11b) (712.44 g, 78%). The instrumental spectrum data and HPLC retention time (Rt) of the obtained compound (11b) were completely consistent with those obtained in Reference Example 5.

Example 5

2-Bromo-5-methyl-4,5,6,7-tetrahydrothiazolo[5,4-c]pyridine mono-p-toluenesulfonate (11b)

[Formula 65]

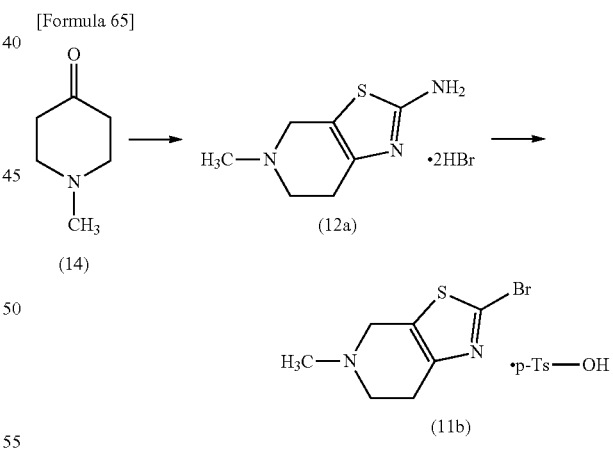

1-Methyl-4-piperidone (14) (300.0 g), cyanamide (245.20 g), sulfur powders (85.02 g), and a catalytic amount of pyrrolidine (18.85 g) were added to 2-propanol (2100 mL) at room temperature, and the mixture was stirred at approximately 50° C. for approximately 3 hours and then concentrated to distil off 2-propanol. To the residue, water (2700 ml) and 48% hydrobromic acid (720 mL) were added, and insoluble matter was collected by filtration to obtain an aqueous solution of 2-amino-5-methyl-4,5,6,7-tetrahydrothiazolo[5,4-c]pyridine dihydrobromide (12a) [381.4 g in terms of free form (12)].

4-Hydroxy-2,2,6,6-tetramethylpiperidine 1-oxyl (TEMPOL) (22.83 g) was added and dissolved in a mixed solution of water (2700 mL) and 48% hydrobromic acid (1080 mL). The mixed solution was cooled to 0 to 5° C., and the aqueous solution of 2-amino-5-methyl-4,5,6,7-tetrahydrothiazolo[5,4-c]pyridine dihydrobromide (12a) [381.4 g in terms of free form (12)] and a solution of sodium nitrite (274.43 g) in water (1500 mL) were simultaneously added dropwise thereto over 2 to 5 hours such that the internal temperature of the reaction solution was kept at 0 to 10° C. under a nitrogen stream in the reaction system. After completion of the dropwise addition, the reaction mixture was further stirred at 0 to 10° C. for 1 hour. The reaction mixture was rendered alkaline (pH>13) by the dropwise addition of a 25% aqueous sodium hydroxide solution (2400 mL) with the internal temperature kept at 20° C. or lower. Subsequently, the reaction mixture was subjected to extraction twice with toluene (3000 mL), and the toluene extract layer was concentrated. To the residue, methanol (600 mL) and toluene (2550 mL) were added, and the mixture was dissolved by stirring at 15 to 35° C. A solution of p-toluenesulfonic acid monohydrate (453.87 g) in methanol (900 mL) was added dropwise thereto at 15 to 35° C. over 30 minutes or longer, and the mixed solution was then cooled to 0 to 5° C. and stirred at 0 to 5° C. for 30 minutes or longer. The precipitated solid was filtered and washed with methanol (1350 mL) cooled to 0 to 5° C. The obtained solid was dried at 40° C. to obtain the title compound (11b) (712.44 g, 78%). The instrumental spectrum data and HPLC retention time (Rt) of the obtained compound (11b) were completely consistent with those obtained in Reference Example 5.

Example 6

5-Methyl-4,5,6,7-tetrahydrothiazolo[5,4-c]pyridine-2-carboxylic acid monohydrochloride (13a)

[Formula 66]

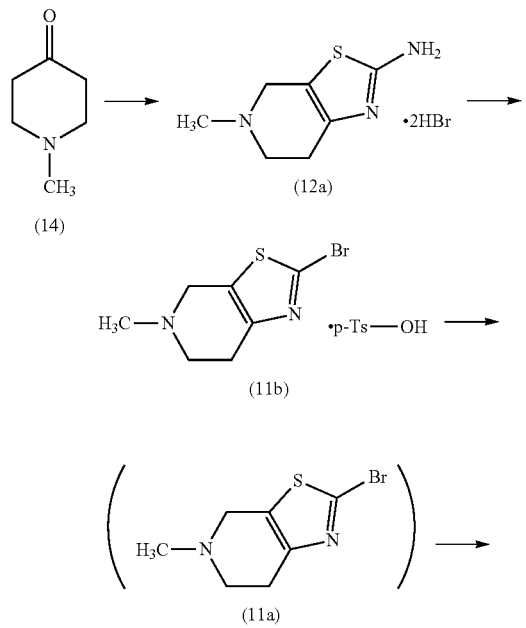

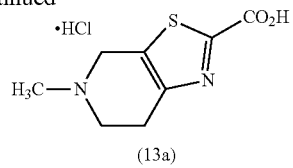

1-Methyl-4-piperidone (14) (300.0 g), cyanamide (245.20 g), sulfur powders (85.02 g), and a catalytic amount of pyrrolidine (18.85 g) were added to 2-propanol (2100 mL) at room temperature, and the mixture was stirred at approximately 50° C. for approximately 3 hours and then concentrated to distil off 2-propanol. To the residue, water (3000 ml) and 48% hydrobromic acid (720 mL) were added, and insoluble matter was collected by filtration to obtain an aqueous solution of 2-amino-5-methyl-4,5,6,7-tetrahydrothiazolo[5,4-c]pyridine dihydrobromide (12a) [381.4 g in terms of free form (12)].

4-Hydroxy-2,2,6,6-tetramethylpiperidine 1-oxyl (TEMPOL) (22.83 g) was added and dissolved in a mixed solution of water (2700 mL) and 48% hydrobromic acid (1080 mL). The mixed solution was cooled to 0 to 5° C., and the aqueous solution of 2-amino-5-methyl-4,5,6,7-tetrahydrothiazolo[5,4-c]pyridine dihydrobromide (12a) [381.4 g in terms of free form (12)] and a solution of sodium nitrite (274.43 g) in water (1500 mL) were simultaneously added dropwise thereto over 2 to 5 hours such that the internal temperature of the reaction solution was kept at 0 to 10° C. under a nitrogen stream in the reaction system. After completion of the dropwise addition, the reaction mixture was further stirred at 0 to 10° C. for 1 hour. The reaction mixture was rendered alkaline (pH>13) by the dropwise addition of a 25% aqueous sodium hydroxide solution (2400 mL) with the internal temperature kept at 20° C. or lower. Subsequently, the reaction mixture was subjected to extraction twice with toluene (3000 mL), and the toluene extract layer was concentrated. To the residue, methanol (600 mL) and toluene (2550 mL) were added, and the mixture was dissolved by stirring at 15 to 35° C. A solution of p-toluenesulfonic acid monohydrate (453.87 g) in methanol (900 mL) was added dropwise thereto at 15 to 35° C. over 30 minutes or longer, and the mixed solution was then cooled to 0 to 5° C. and stirred at 0 to 5° C. for 30 minutes or longer. The precipitated solid was filtered and washed with methanol (1350 mL) cooled to 0 to 5° C. The obtained solid was dried at 40° C. to obtain the compound (11b) (712.44 g, 78%). The instrumental spectrum data and HPLC retention time (Rt) of the obtained compound (1b) were completely consistent with those obtained in Reference Example 5.

Compound (11b) (712.44 g) thus obtained was treated with a 1 M aqueous sodium hydroxide solution (3562 ml) at 30° C. or lower, followed by extraction with toluene (twice). The combined extract was washed with 5% sodium chloride (3562 ml) at 30° C. or lower, and the organic layer was then concentrated under reduced pressure until the amount of the solvent remaining became approximately 1500 ml so that the resulting solution had a water content of 0.1% or less. To this solution, tetrahydrofuran (4275 ml) was added, and the mixture was cooled to an internal temperature of −70° C. or lower with stirring under a nitrogen stream. To this solution, n-butyl lithium (used as a 17.22% solution in n-hexane) (673.49 g) was added with the internal temperature kept at −70° C. or lower. After completion of the addition, the reaction mixture was stirred at an internal temperature of −70° C. or lower for 30 minutes to 1 hour [this mixed solution was subjected to sampling, and the amount of compound (11a) remaining was confirmed by HPLC to be less than 0.1%]. To the reaction mixture, gaseous carbon dioxide (carbonic acid gas) (154.7 g to 200 g) was introduced with the internal temperature kept at −70° C. or lower. After completion of the introduction of carbon dioxide, the reaction solution was stirred at an internal temperature of −65° C. or lower for 1 hour longer, and the internal temperature of the reaction solution was subsequently raised to approximately −20° C. Methanol (2850 ml) was added to the reaction solution at an internal temperature of −20 to 5° C., and water (356 ml) and methanol (712 ml) were subsequently added in this order thereto with the internal temperature kept in the range of −5 to 5° C. Concentrated hydrochloric acid (356 ml) was added dropwise to the reaction mixture with the internal temperature kept in the range of 0 to 10° C. After completion of the dropwise addition, the reaction mixture was cooled again to an internal temperature of 0 to 5° C. and stirred at this temperature for 1 hour or longer. The precipitated crystals were collected by filtration, washed with methanol/toluene (½, 2137 ml) cooled to 0 to 5° C. in advance, and then dried at 30° C. to obtain the title compound (13a) [371.28 g, yield based on compound (14): 60%; yield based on compound (11b): 90%. Various instrumental spectrum data and HPLC retention time (Rt) of the obtained compound (13a) were consistent with those of Preparation Examples 14 and 15 described in International Publication No. WO 2005/047296.

Industrial Applicability

The present invention provides a novel process for preparing a substituted aromatic compound such as an aromatic halo compound salt using a nitroxide radical compound. The preparation process of the present invention is highly versatile and offers high yields. The preparation process of the present invention is also suitable for large-scale synthesis and as such, can be used as an industrial process for preparing an intermediate for pharmaceutical preparation.

The invention claimed is:

1. A process for preparing a compound represented by the following formula (11a) or a salt or a solvate thereof:

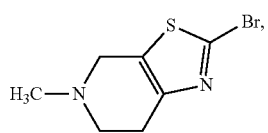

(11a)

the process comprising:
adding a nitroxide radical compound to an aqueous solution of a hydrobromic acid to prepare a solution, which is then cooled to 10° C. or lower and stirred; and
simultaneously adding the following (a) and (b) into the solution at 10° C. or lower:
(a) an aqueous solution of a compound represented by the following formula (12) or a salt or a solvate thereof:

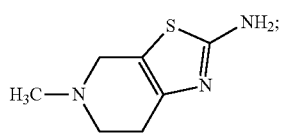

(12)

and
(b) an aqueous solution of a diazotization reagent.

2. The preparation process according to claim 1, wherein the compound represented by formula (12) or a salt or a solvate thereof is a hydrobromide of the compound represented by formula (12).

3. The preparation process according to claim 2, wherein the hydrobromide of the compound represented by formula (12) is a dihydrobromide compound represented by the following formula (12a) or a hydrate of the salt:

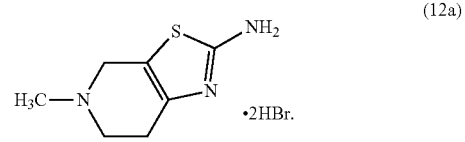

(12a)

4. The preparation process according to claim 1, wherein the diazotization reagent is an alkali metal nitrite or an alkaline earth metal nitrite.

5. The preparation process according to claim 1, wherein the step of simultaneously adding (a) and (b) into the solution at 10° C. or lower comprises simultaneously adding (a) and (b) in the range of 2 to 10 hours.

6. A preparation process according to claim 5, wherein in the simultaneous addition step, the completion time lag between the addition of (a) and the addition of (b) is within 1 hour.

7. The preparation process according to claim 1, wherein the step of simultaneously adding (a) and (b) into the solution at 10° C. or lower is performed under an inert gas atmosphere.

8. The preparation process according to claim 7, wherein the inert gas is nitrogen or argon.

9. A process for preparing a compound represented by the following formula (11b):

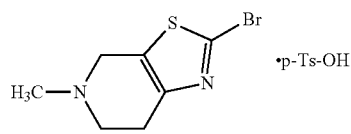

(11b)

the process comprising:
adding and dissolving a nitroxide radical compound in an aqueous solution of hydrobromic acid to prepare a solution, which is then cooled to 10° C. or lower and stirred;
simultaneously adding the following (a) and (b) into the solution at 10° C. or lower under a nitrogen or argon gas atmosphere:
(a) an aqueous solution of a compound represented by the following formula (12a) or a hydrate of the salt:

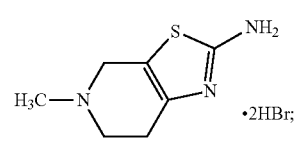

(12a)

and
(b) an aqueous solution of an alkali metal nitrite or an alkaline earth metal nitrite;
and
subsequently neutralizing the resulting compound with an aqueous alkali solution, followed by treatment with p-toluenesulfonic acid to obtain the compound represented by formula (11 b).

10. A process for preparing a compound represented by the following formula (13a):

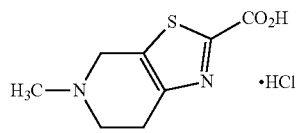

the process comprising:
adding and dissolving a nitroxide radical compound in an aqueous solution of hydrobromic acid to prepare a solution, which is then cooled to 10° C. or lower and stirred; and
simultaneously adding the following (a) and (b) into the solution at 10° C. or lower under a nitrogen or argon gas atmosphere:
(a) an aqueous solution of a compound represented by the following formula (12a) or a hydrate thereof:

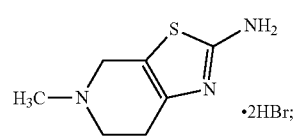

and
(b) an aqueous solution of an alkali metal nitrite or an alkaline earth metal nitrite, and
subsequently neutralizing the resulting compound with an aqueous alkali solution, followed by treatment with p-toluenesulfonic acid to obtain a compound represented by the following formula (11 b):

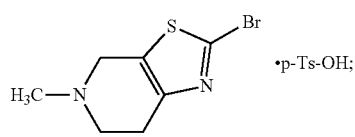

and
neutralizing the compound represented by formula (11b) with alkali, followed by treatment with an alkyl lithium and carbon dioxide and further treatment with hydrochloric acid to obtain the compound represented by formula (13a).

11. The preparation process according to claim 10, wherein the alkyl lithium is n-butyl lithium.

12. The preparation process according to claim 1, wherein the nitroxide radical compound is one or two or more compounds selected from the group consisting of the following:
3-carboxy-2,2,5,5-tetramethyl-1-pyrrolidine 1-oxyl;
3-carbamoyl-2,2,5,5-tetramethylpyrrolidine 1-oxyl;
3-carbamoyl-2,2,5,5-tetramethyl-3-pyrroline 1-oxyl;
4-oxo-2,2,6,6-tetramethylpiperidinoxyl;
4-hydroxy-2,2,6,6-tetramethylpiperidine 1-oxyl;
4-acetamido-2,2,6,6-tetramethylpiperidine 1-oxyl;
2,2,6,6-tetramethylpiperidine 1-oxyl;
3-(maleimidomethyl)-proxyl;
N-(1-oxyl-2,2,6,6-tetramethyl-4-piperidinyl)maleimide; and 1-methyl-2-azaadamantane N-oxyl;
and salts thereof.

13. The preparation process according to claim 1, wherein the amount of the nitroxide radical compound used is stoichiometrically in the range of 0.01 to 0.5 molar equivalents with respect to compound (12).

14. A process for preparing a compound represented by the following formula (E-a):

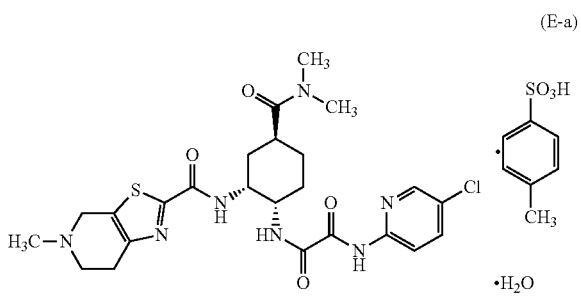

comprising using compound (13a) prepared using a preparation process according to claim 10, the process comprising the steps of:
deprotecting a Boc group in a compound represented by the following formula (17):

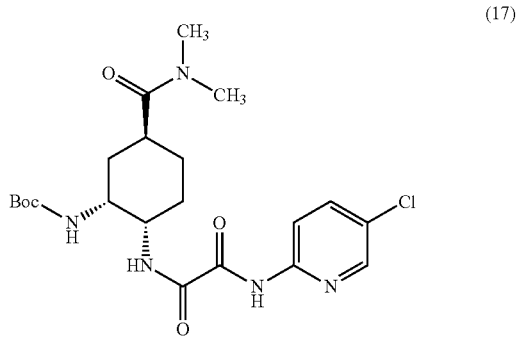 [SMILES: CN(C)C(=O)[C@H]1CC[C@H](NC(=O)C(=O)Nc2ccc(Cl)cn2)[C@H](NC(=O)OC(C)(C)C)C1]

wherein Boc represents a tert-butoxycarbonyl group,
and then condensing the resulting compound with a compound represented by the following formula (13a):

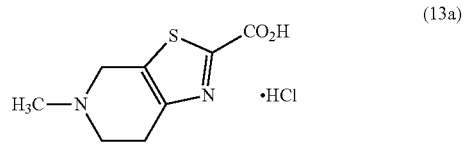

in the presence of a base to obtain a compound represented by the following formula (E):
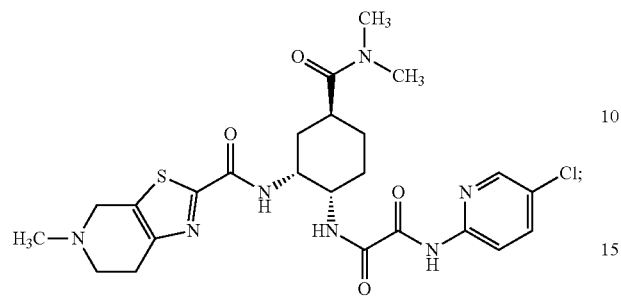
(E)
and
treating the compound represented by formula (E) with p-toluenesulfonic acid or a hydrate thereof in aqueous alcohol to obtain the compound represented by formula (E-a).
* * * * *